US007617116B2

(12) United States Patent
Amar et al.

(10) Patent No.: US 7,617,116 B2
(45) Date of Patent: Nov. 10, 2009

(54) PRACTICE MANAGEMENT AND BILLING AUTOMATION SYSTEM

(75) Inventors: Anshul Amar, Brooklyn, NY (US); Steve Stone, Arlington, MA (US); Ed Park, Hamden, CT (US); Todd Park, Waltham, MA (US)

(73) Assignee: athenahealth, Inc., Watertown, MA (US)

( * ) Notice: Subject to any disclaimer, the term of this patent is extended or adjusted under 35 U.S.C. 154(b) by 870 days.

(21) Appl. No.: 09/921,654

(22) Filed: Aug. 3, 2001

(65) Prior Publication Data

US 2002/0133503 A1    Sep. 19, 2002

Related U.S. Application Data

(60) Provisional application No. 60/223,235, filed on Aug. 4, 2000.

(51) Int. Cl.
*G06Q 40/00* (2006.01)
(52) U.S. Cl. .............................................. 705/4; 705/3
(58) Field of Classification Search ................... 705/34, 705/2–4, 8, 51, 40, 7; 709/203, 223; 707/104.1, 707/102
See application file for complete search history.

(56) References Cited

U.S. PATENT DOCUMENTS

| | | | |
|---|---|---|---|
| 4,491,725 A | 1/1985 | Pritchard | 235/375 |
| 4,831,526 A | 5/1989 | Luchs et al. | |
| 4,858,121 A | 8/1989 | Barber et al. | |
| 5,070,452 A | 12/1991 | Doyle, Jr. et al. | |
| 5,225,976 A | 7/1993 | Tawil | |
| 5,235,507 A | 8/1993 | Sackler et al. | |
| 5,235,702 A * | 8/1993 | Miller | 707/102 |
| 5,253,164 A | 10/1993 | Holloway et al. | |
| 5,301,105 A | 4/1994 | Cummings, Jr. | |

(Continued)

FOREIGN PATENT DOCUMENTS

EP    0683465 A2    11/1995 ............... 17/60

(Continued)

OTHER PUBLICATIONS

Borzo, "The Newspaper for America's Physicians," Amednews.com, Aug. 11, 1997, pp. 1-3; available at: http://www.ama-assn.org/sci-pubs/amnews/net_97/log0811.htm, (last visited May 22, 2003).

(Continued)

*Primary Examiner*—Natalie A Pass
(74) *Attorney, Agent, or Firm*—Proskauer Rose LLP

(57) ABSTRACT

A medical practice management system can be used to manage a medical practice. A medical practice management server communicates with a medical practice client user interface over a first network and communicates with a payor server over a second network. The medical practice management server receives information associated with a visit by a patient to the medical practice. Prior to using the information to create a claim, the medical practice management server automatically and repeatedly interacts with the information to ensure correct information by either applying one or more rules to the information or by performing one or more transactions with the payor server. The medical practice management server performs a correcting action in response to finding an error in the information and subsequently uses the information to create an insurance claim.

20 Claims, 22 Drawing Sheets

U.S. PATENT DOCUMENTS

| | | | |
|---|---|---|---|
| 5,325,290 A | | 6/1994 | Cauffman et al. |
| 5,359,509 A | | 10/1994 | Little et al. |
| 5,519,607 A | | 5/1996 | Tawil |
| 5,523,942 A | | 6/1996 | Tyler et al. |
| 5,560,008 A | | 9/1996 | Johnson et al. |
| 5,644,778 A | | 7/1997 | Burks et al. |
| 5,696,906 A | | 12/1997 | Peters et al. |
| 5,704,044 A | * | 12/1997 | Tarter et al. ............... 705/4 |
| 5,715,397 A | | 2/1998 | Ogawa et al. |
| 5,721,908 A | | 2/1998 | Lagarde et al. |
| 5,790,548 A | | 8/1998 | Sistanizadeh et al. |
| 5,794,221 A | | 8/1998 | Egendorf |
| 5,832,460 A | | 11/1998 | Bednar et al. |
| 5,852,812 A | | 12/1998 | Reeder |
| 5,864,683 A | | 1/1999 | Boebert et al. |
| 5,884,284 A | | 3/1999 | Peters et al. |
| 5,886,693 A | | 3/1999 | Ho et al. ............... 345/335 |
| 5,903,873 A | | 5/1999 | Peterson et al. |
| 5,911,132 A | | 6/1999 | Sloane |
| 5,915,241 A | | 6/1999 | Giannini |
| 5,920,847 A | | 7/1999 | Kolling et al. |
| 5,924,074 A | | 7/1999 | Evans |
| 5,924,090 A | | 7/1999 | Krellenstein |
| 5,930,759 A | | 7/1999 | Moore et al. |
| 5,958,016 A | | 9/1999 | Chang et al. |
| 5,974,389 A | | 10/1999 | Clark et al. ............... 705/3 |
| 5,995,939 A | * | 11/1999 | Berman et al. ............... 705/3 |
| 5,999,941 A | | 12/1999 | Andersen |
| 5,999,973 A | | 12/1999 | Glitho et al. |
| 6,003,007 A | | 12/1999 | DiRienzo |
| 6,012,035 A | | 1/2000 | Freeman, Jr. et al. |
| 6,023,684 A | | 2/2000 | Pearson |
| 6,044,362 A | * | 3/2000 | Neely ............... 705/34 |
| 6,047,259 A | * | 4/2000 | Campbell et al. ............... 705/3 |
| 6,052,674 A | | 4/2000 | Zervides et al. |
| 6,092,055 A | | 7/2000 | Owens et al. |
| 6,112,183 A | | 8/2000 | Swanson et al. |
| 6,138,150 A | | 10/2000 | Nichols et al. |
| 6,151,581 A | | 11/2000 | Kraftson et al. ............... 705/3 |
| 6,199,115 B1 | | 3/2001 | DiRienzo ............... 709/236 |
| 6,208,973 B1 | * | 3/2001 | Boyer et al. ............... 705/2 |
| 6,208,974 B1 | | 3/2001 | Campbell et al. ............... 705/3 |
| 6,223,213 B1 | | 4/2001 | Cleron et al. |
| 6,285,991 B1 | | 9/2001 | Powar |
| 6,304,857 B1 | | 10/2001 | Heindel et al. |
| 6,343,271 B1 | * | 1/2002 | Peterson et al. ............... 705/4 |
| 6,345,260 B1 | * | 2/2002 | Cummings et al. ............... 705/8 |
| 6,374,229 B1 | * | 4/2002 | Lowrey et al. ............... 705/34 |
| 6,453,297 B1 | * | 9/2002 | Burks et al. ............... 705/3 |
| 6,738,784 B1 | * | 5/2004 | Howes ............... 707/104.1 |
| 6,757,898 B1 | * | 6/2004 | Ilsen et al. ............... 709/203 |
| 6,879,959 B1 | * | 4/2005 | Chapman et al. ............... 705/2 |
| 6,947,907 B1 | * | 9/2005 | Silverman ............... 705/40 |
| 7,016,856 B1 | * | 3/2006 | Wiggins ............... 705/2 |
| 2001/0027403 A1 | * | 10/2001 | Peterson et al. ............... 705/4 |
| 2002/0010679 A1 | * | 1/2002 | Felsher ............... 705/51 |
| 2002/0022972 A1 | * | 2/2002 | Costello ............... 705/2 |
| 2002/0035488 A1 | * | 3/2002 | Aquila et al. ............... 705/2 |
| 2002/0046165 A1 | * | 4/2002 | Kitchen et al. ............... 705/40 |
| 2002/0049617 A1 | * | 4/2002 | Lencki et al. ............... 705/4 |
| 2002/0077849 A1 | * | 6/2002 | Baruch et al. ............... 705/2 |
| 2002/0120473 A1 | * | 8/2002 | Wiggins ............... 705/4 |
| 2003/0208379 A1 | * | 11/2003 | Haskey et al. ............... 705/2 |

FOREIGN PATENT DOCUMENTS

| | | | | |
|---|---|---|---|---|
| EP | | 0809830 B1 | 12/1997 | ............... 17/30 |
| WO | | 00/03343 | 1/2000 | ............... 17/60 |
| WO | | 00/67173 | 11/2000 | ............... 17/60 |

OTHER PUBLICATIONS

Author unknown, "Medical Services, 7 Steps to Internet Claims Processing," Claimsnet.com, p. 1, available at: http://www.web.archive.org/web/19980109111742/claimsnet.com/html/medical_services.htm; (last visited on May 19, 2003.

Author unknown, "Millbrook and Claimsnet.com Partner to Deliver Integrated Healthcare Transaction Processing Solution," Millbrook, Apr. 6, 1998, pp. 1-2; available at: http://www.millbrook.com/viewnews.asp?articleID=4, (last visited May 22, 2003).

Author unknown, "News & Press Releases," Claimsnet.com, p. 1; available at: http://web.archive.org/web/19990219095552/www.claimsnet.com/pressrelease/, (last visited May 19, 2003).

Author unknown, "Questions about Claimsnet," Claims.net, pp. 1-3; available at: http://web.archive.org/web/19980112180942/www.claimsnet.com/html/claimsnet.com_questions.htm (last visited on Nov. 14, 2003).

Author unknown, "Questions About Payors," Claimsnet.com, pp. 1-3; available at: http://web.archive.org/web/199905011 61227/www.claimsnet.com/public/payor_questions.asp, (last visited Nov. 14, 2003).

Author unknown, "Miscellaneous Questions," Claimsnet.com, pp. 1-3; available at: http://web.archive.org/web/19990501174525/www.claimsnet.com/public/troubleshooting_questions, (last visited Nov. 14, 2003).

Author unknown, "About Claimsnet.com," Claimsnet.com, undated, pp. 1-3.

Author unknown, "Questions about the Claims Processing Software," Claimsnet.com, pp. 1-4; available at: http://web.archive.org/web/19990501150341/www.claimsnet.com/public/claim_processing_question, (last visited Nov. 14, 2003).

Author unknown, "Premier Subsidiary Awards Claimsnet.com Contract to Offer Internet Claims Processing," Claimsnet.com, Oct. 26, 1998, pp. 1-2; available at: http://web.archive.org/web/19990220055929/www.claimsnet.com/pressrelease/102698.asp, (last visited Nov. 14, 2003).

Author unknown, "Instructions for Downloading Software," Claimsnet.com, pp. 1-2; available at: http://web.archive.org/web/1999050111558859/www.claimsnet.com/public/instructions.asp, (last visited Nov. 14, 2003).

Author unknown, "About Your HCFA-1500 Claims," Claimsnet.com, pp. 1-2; available at: http://web.archive.org/web/19970411064021/www.claimsnet.com/html/about_hefa-1500.htm, (last visited Nov. 14, 2003).

Author unknown, "Easy Fast Safe Free," Claimsnet.com, p. 1; available at: http:/web.archive.org/web/19970411062518/www.claimsnet.com/html/easy_fast_safe_free.htm, (last visited Nov. 14, 2003).

Author unknown, "Reimbursement Management Services," Claimsnet.com, p. 1; available at: http://web.archive.org/19970411062719/www.claimsnet.com/html/other_services.htm, (last visited Nov. 14, 2003).

Author unknown, "Medical Services,"Claimsnet.com, p. 1; available at: http://web.archive.org/web/19970411062445/www.claimsnet.com/html/medical_services.htm, (last visited Nov. 14, 2003).

Author unknown, "Sample Claims," Claimsnet.com, p. 1; available at: http://web.archive.org/web/19970411063339/www.claimsnet.com/html/sample_claims.htm, (last visited Nov. 14, 2003).

Author unknown, "Medical Pricing Guide," Claimsnet.com, p. 1; available at: http://web.archive.org/web/19970411063509/www.claimsnet.com/html/medical_pricing.htm, (last visited Nov. 14, 2003).

Author unknown, "7 Easy steps to processing claims over the Internet," Claimsnet.com, p. 1; available at: http://web.archive.org/web/19970411062637/www.claimsnet.com/html/7_easy_steps.htm, (last visited Nov. 14, 2003).

Author unknown, "Corporate History and Mission," Claimsnet.com, pp. 1-2; available at: http:/web.archive.org/web/19970411062906/www.claimsnet.com/html/corporate_history.htm, (last visited Nov. 14, 2003).

Author unknown, "Questions about claimsnet.com," Claimsnet.com, pp. 1-3; available at: http://web.archive.org/web/19970411063301/http://www.claimsnet.com/html;claimsnet.com_question, (last visited Nov. 14, 2003).

Author unknown, "The Transaction Network," Healtheon Corporation, p. 1; available at: http://web.archive.org/19980203083010/www.healtheon.com/htmldocs/proddemo8.html, (last visited May 20, 2003).

Author unknown, "About Our Customers," Healtheon Corporation, p. 1; available at: http://web.archive.org/web/19980203081059/www.healtheon.com/htmldocs/clients.html,: (last visited May 20, 2003).

Author unknown, "Internet-based enterprise solutions for healthcare," Healtheon Corporation, p. 1; available at: http://web.archive.org/web/19980203081225/ww.healtheon.com/index.html, (last visited May 20, 2003).

Author unknown, "Market Challenge," Healtheon Corporation, pp. 1-4; available at: http://web.archive.org/web/19990422184238/www.healtheon.com/phys/index.html, (last visited May 20, 2003).

Author unknown, "Services," Healtheon Corporation, pp. 1-5; available at: http://web.archive.org/web/19990427191257/www.healtheon.com/phys/phys_ser.html, (last visited May 20, 2003).

Author unknown, "Healtheon Services and Solutions," Healtheon Corporation, pp. 1-8; available at: http://web.archive.org/web/1999042219422194152/http://www.healtheon.com/services/index.html, (last visited May 20, 2003).

Author unknown, "The Next Generation in Healthcare Information Management," Healtheon Corporation, pp. 1-5; available at: http://web.archive.org/web/19990422203244/www.healtheon.com/tech/index.html, (last visited May 20, 2003).

Author unknown, "Provider Services, Services for Physicians and Integrated Delivery Systems," Healtheon Corporation, pp. 1-2; available at: http://web.archive.org/web/19980203081357/www.healtheon.com/htmldocs/clients-pp.html, (last visited May 20, 2003).

Shepard, "IDXchange, Technology for the Future," IDX Systems Corporation, Summer 1997, pp. 1-8.

Author unknown, "IDX Systems Corporation Announces Healthcare Internet Solution," IDX Systems Corporation, pp. 1-2; available at: http://web.archive.org/web/19970821150641/www.idx.com/aboutid/press_releases/outreach, (last visited May 15, 2003).

Author unknown, "Billing and Accounts Receivable (BAR)," IDX Systems Corporation, p. 1; available at: http://web.archive.org/web/19961106115029/www.idx.com/products/bar.htm, (last visited May 15, 2003).

Author unknown, "Group Practice Management System, IDX Product Information, Group Practice Management Systems (GPMS)," IDX Systems Corporation, p. 1; available at: http://web.archive.org/web/19961106115151/www.idx.com/products/gpms.htm, (last visited May 15, 2003).

Author unknown, "IDX Takes the Lead in Healthcare Billing," IDX Systems Corporation, pp. 1-2; available at: http://web.archive.org/web/19970821150544/www.idx.com/aboutidx/press_releases/imper..., (last visited May 20, 2003).

Author unknown, "IDX Systems Corporation Announces Agreement with Citrix Systems," IDX Systems Corporation, pp. 1-2; available at: http://web.archive.org/web/19970821150557/www.idx.com/aboutidx/press_releases/citrix, (last visited May 15, 2003).

Author unknown, "IDX Systems Corporation and Medpartners, Inc. Team Up to Provide IPA Doctors with Internet Connectivity," DX Systems Corporation, pp. 1-2; available at: http://web.archive.org/web/19970821150616/www.idx.com/aboutidx/press_releases/medpartners, (last visited May 15, 2003).

Author unknown, "IDX Systems Corporation and Envoy Corporation Sign Agreement," IDX Systems Corporation, p. 1; available at: http://web.archive.ocr/web/19970821150656/www.idx.com/aboutidx/press_releases/envoy, (last visited May 15, 2003).

Author unknown, "The IDXtend Solution," IDX Systems Corporation, pp. 1-2; available at: http://web.archive.org/web/19961106113320/www.idx.com/idxtend/index.htm, (last visited May 15, 2003).

Author unknown, "IDXtend: Ambulatory Suite, Billing and Accounts Receivable," IDX Systems Corporation, pp. 1-2; available at: http://web.archive.org/web/19961106113503/www.idx.com/idxtend/bar.htm, (last visited May 15, 2003).

Author unknown, "IDXtend: Ambulatory Suite, IDXtendTM Ambulatory Suite," IDX Systems Corporation, pp. 1-2; available at: http://web.archive.org/web/19961106113330/www.idx.com/idxtend/ambulatory.htm, (last visited May 15, 2003).

Author unknown, "IDXtend: Extension Architecture: Electronic Data Interchange," IDX Systems Corporation, pp. 1-2; available at: http://web.archive.org/web/1996113409/www.idx.com/idxtend/edi.htm, (last visited May 15, 2003).

Author unknown, "IDXtend: Extension Architecture," IDX Systems Corporation, pp. 1-2; available at: http://web.archive.org/web/19961106113446/www.idx.com/idxtend/extension_arch.htm, (last visited May 15, 2003).

Author unknown, "IDXtend: Ambulatory Suite, Financial Management," IDX Systems Corporation, p. 1; available at: http://web.archive.org/web/19961106113456/www.idx.com/idxtend/fin_management.htm, (last visited May 15, 2003).

Davis, "No paper trail: Computerized health claims system nears debut," Telephony.online, Feb. 2, 1998, pp. 1-2; available at: http://telephonyonline.com/ar/telecom_no_paper_trail/, (last visited May 22, 2003).

Author unknown, "Corporate Profile for RealMed," Business Wire, Apr. 3, 1998, pp. 1-2; available at: http://www.businesswire.com/webbox/bw.040398/651707.htm, (last visited May 22, 2003).

Author unknown, "The Medical Manager Version Nine: Electronic Communications" The Medical Manager, pp. 1-6; available at: http://web.archive.org/web/19990220072207/www.medicalmanager.com/v9/003.htm, (last visited May 15, 2003).

Author unknown, "EDI Solution," The Medical Manager, pp. 1-6; available at: http://web.archive.org/web/19981203051009/www.medicalmanager.com/overvu/edicoln.htm, (last visited May 19, 2003).

Author unknown, "Medical Manager Corporation and ENVOY Corporation Announce Strategic Alliance for Enhanced EDI Services," The Medical Manager, pp. 1-2; available at: http://web.archive.org/web/19980116102745/www.medicalmanager.com/press/press14.htm, (last visited May 15, 2003).

Author unknown, "The Medical Manager Version Nine: Meeting Special Needs," The Medical Manager, pp. 1-5; available at: http://web.archive.org/web/19990220153158/www.medicalmanager.com/v9/009.htm, (last visited May 15, 2003).

Author unknown, "The MedicalManager Version Nine: Sharing Medical Information," The Medical Manager, pp. 1-4; available at: http://web.archive.org/web/19990220134426/www.medicalmanager.com/v9/008.htm, (last visited May 15, 2003).

Author unknown, "Millbrook Corporation, Case Study II," Millbrook Corporation, pp. 1-2; available at: htpp:/web.archive.org/web/19981206120908/www.millbrook.com/Millbrook/csl 1.htm, (last visited May 15, 2003).

Author unknown, "Millbrook Paradigm Case Study 1, Wise County Medical & Surgical Association," Millbrook Corporation, pp. 1-2; available at: http://web.archive.org/web/19970703191143/www.millbrook.com/csl.htm, (last visited May 15, 2003).

Author unknown, "Millbrook Paradigm Case Study 2 Cascade Healthcare Alliance," Millbrook Corporation, pp. 1-2; available at: http://web.archive.org/web/19970703191151/www.millbrook.com/cs2.htm, (last visited May 15, 2003).

Author unknown, "Millbrook Paradigm- Products," Millbrook Corporation, p. 1; available at: http://web.archive.org/web/19970703190425/www.millbrook.com/prod.htm, (last visited May 15, 2003).

Voreis, "Humana Partners with Kinetra for Comprehensive Physician Connectivity Initiative," Kinetra LLC, pp. 1-4; available at: http://web.archive.org/web/19990203112041/www.kinetra.com/news/News_Humana/ne, (last visited May 20, 2003).

Voreis, "St. Joseph to Electronically Link Physicians, Hospital," Kinetra LLC, pp. 1-3; available at: http://web.archive.org/web/19990427180501/www.kinetra.com/news/News_St._Joseph/n, (last visited May 20, 2003).

Author unknown, "Our Mission," Kinetra LLC, pp. 1-2; available at: http://web.archive.org/web/19981111184324/http://www.kinetra.com/, (last visited May 20, 2003).

Voreis, "EDI-USA and Kinetra Establish Payer-Provider Connectivity," Kinetra LLC, pp. 1-3; available at: http://web.archive.org/web/19990203093836/www.kinetra.com/news/News_EDI-USA/n, (last visited May 20, 2003).

Voreis, "EDS and Lilly Announce the Formation of Kinetra," Kinetra LLC, pp. 1-4; available at: http://web.archive.org/web/20010506123316/www.kinetra.com/news/news_kinetra.html, (last visited May 20, 2003).

Voreis, "Kinetra Announces General Release of Radiant for Windows 2.00," Kinetra LLC, pp. 1-2; available at: http://web.archive.org/web/19990427174526/www.kinetra.com/news/News_Radiant_2.00, (last visited May 20, 2003).

Author unknown, "About Kinetra," Kinetra LLC, pp. 1-11; available at: http://web.archive.org/web/19990203035019/www.kinetra.com/About_Kinetra/about_kinetra, (last visited May 20, 2003).

Greenberg, "Putting Information Where it Works," Advance Online Editions, Merion Publications, Aug. 1, 1997, pp. 1-5.

Author unknown, "Sounding Board—Thin Client Technology Gains Momentum," Advance Online Editions, Merion Publications, Apr. 1, 1998, pp. 1-4.

Wenzlick, "Hot at HIMSS," Advance Online Editions, Merion Publications, Mar. 1, 1998, pp. 1-7.

Thomas, "Creative Thinking with Thin-Client/Server Technology," Advance Online Editions, Merion Publications, Nov. 1, 1998, pp. 1-4.

Author unknown, "Lawson, IBM Sell Nation's First 'All-Network' Healthcare Solution, Good Samaritan pays $2 Million for 100% Browser-Based Software," Lawson Software, pp. 1-2; available at: http://web.archive.org/web/19991110130038/www.lawson.com/4news/1998/00jan98/good, (last visited May 19, 2003).

Author unknown, "The Lawson Software Strategy for Healthcare Cost Management," Lawson Software, 1996, pp. 1-8.

Author unknown, "Lawson Insight Business Management System—Supply Chain Process Suite," Lawson Software, 1996, pp. 1-10; available at: http://web.archive.org/web/19970712130558/http://www.lawson.com/3prod/lovervw/4supply/default . . . , (last visited Nov. 7, 2003).

Author unknown, "Lawson Releases Next Generation of Java Deployability for Lawson Insight," Lawson Software, pp. 1-2; available at: http://web.archive.org/web/19991007042731/www.lawson.com/4news/1998/00apr98/java/default.htm, (last visited Nov. 7, 2003).

Author unknown, "Enterprise Process Management through Workflow," Lawson Software, 1996, pp. 1-10; available at: http://web.archive.org/web/19970712132213/www.lawson.com/3prod/2techovr/techwite/2entproc/def (last visited Nov. 17, 2003).

Author unknown, "Aberdeen Group Product Viewpoint—Lawson Software Delivers the Desktop and Workflow Combination One-Two-Punch," Lawson Software, vol. 9, No. 1, Jan. 12, 1996, pp. 1-10; available at: http://web.archive.org/web/19980524232743/www.lawson.com/3prod/2techovr/aberdf2/default.htm, (lasts visited Nov. 6, 2003).

Author unknown, "Providing Insight to Businesses for More than 20 Years," Lawson Software, 1997, pp. 1-10; available at: http://web.archive.org/web/19980524231732/www.lawson.com/1who/2compovr/default.htm, (last visited Nov. 6, 2003).

Author unknown, "Electronic Commerce Group," HBO & Company, 1997, pp. 1-4; available at: http://web.arachive.org/web/19980202141809/www.hboc.com/network/ecg.htm, (last visited May 19, 2003).

Author unknown, "HBOC's Practice 2000," HBO & Company, 1998, pp. 1-5; available at: http://web.archive.org/web/19980202142540/www.hboc.com/product/cpm/p2000.htm, (last visited May 19, 2003).

Author unknown, "Clinical/Practice Management," HBO & Company, 1997 p. 1; available at: http://web.archive.org/web/19980202141641/www.hboc.com/product/cpm/cpm.htm, (last visited May 19, 2003).

Author unknown, "Services," HBO & Company, 1996 p. 1; available at: http://web.archive.org/web/19980202141909/www.hboc.com/outsourc.out100.htm, (last visited May 19, 2003).

Author unknown, "Connect Technology Group," HBO & Company, 1997 pp. 1-10; available at: http://web.archive.org/web/19980202141837/www.hboc.com/network/ctg.htm, (last visited May 19, 2003).

Author Unknown, Health Management Technology, submissions made in Aug. 1998 issue, 5 pages.

Schneider, "Net Commerce Development Grows," Healthcare Informatics, Sep. 1997, available at http://www.healthcare-informatics.com/issues/1997/09_97/net.htm, (last visited May 22, 2003).

Author Unknown, Health Management Technology, submissions made in May 1998 issue, 6 pages.

FlexBen Corporation, "ReFlexions Monthly Newsletter," vol. VI, No. 3, Mar. 1998.

Capobiano et al., "Looking for Convenient Alternatives to forms for querying remote databases on the Web: a new iconic interface for progressive queries," Dipartimento di Informatica e Sistemistica, Universitàdi Pavia, 1996, pp. 119-124.

Youngworth, "Data analysis across the web: US Army saves $28 million in three years using SAS," e-Business Advisor, Jul. 1998, pp. 20-24.

Luxenberg et al., "Electronic Forms: Benefits and Drawbacks of a World Wide Web-Based Approach to Data Entry," The Official Journal of the American Medical Informatics Association, Hanley & Belfus, Inc., 1997, pp. 804-808.

Elliott, "Healthcare Financials, A diverse group of providers," Healthcare Informatics, Jun. 1998, pp. 105-136.

Healthcare Information Programs, "Industry Report—Internet Technologies in Healthcare," 1999.

Healthcare Informatics, Healthcare Information Programs, "Industry Report—Internet Technologies" 2000.

Author unknown, "PeopleSoft Web Client," PeopleSoft, undated, p. 1.

Author unknown, "PeopleSoft Distribution," PeopleSoft, undated, pp. 1-7.

Author unknown, "The Criteria for Application Usability," Elysium Field Notes, vol. 7, Jul. 1997, pp. 1-4.

Author unknown, "Imagine . . . " Elysium Brochure, Axolotl Corp., 1996, 10 pgs.

Axolotl Corp., "Elysium Workstation," Jul. 24, 1997, 2 pgs. available at, http://www.axolotl.com/axosite.nsf/d7ec08a6a0b033b68825648a00593ed6/3a732eabf31865a10825649d008322aa?OpenDocument.

Axolotl Corp., "Elysium Clinical Information Manager," Jul. 24, 1997, 1 pg., available at, http://www.axolotl.com/axosite.nsf/d7ec08a6a0b033b68825648a00593ed6/518bb8ed60ce9bb40825649d0083956c?OpenDocument.

Author unknown, "Elysium Presentation. Introduction to the Elysium Network," Axolotl Corp., Jul. 24, 1997, 1 pg.; available at: http://www.axolotl.com/Axweb.nsf/dflcb3e4a5eb7c9788256373007c67dd/6acbl1b816ac2b62882563c5006468d2?OpenDocument.

Author unknown, "Elysium Presentation. The Elysium Network," Axolotl Corp., Jul. 24, 1997, 1 pg.; available at: http://www.axolotl.com/Axweb.nsf/dflcb3e4a5eb7c9788256373007c67dd/90d36f74c17289f0882563c7005a5034?OpenDocument.

Author unknown, "Elysium Presentation. The Master Patient Index," Axolotl Corp., Jul. 24, 1997, 1 pg.; available at: http://www.axolotl.com/Axweb.nsf/dflcb3e4a5eb7c9788256373007c67dd/8ad4905759996b63882563c80005fabb?Open Document.

Author unknown, "Elysium Presentation. Introduction to the Patient Locator," Axolotl Corp., Jul. 24, 1997, 2 pgs.; available at: http://www.axolotl.com/Axweb.nsf/dflcb3e4a5eb7c9788256373007c67dd/01260e167eb314a4882563c60004f814?Open Document.

Author unknown, "Elysium Presentation. Viewing Patient Information," Axolotl Corp., Jul. 24, 1997, 1 pg.; available at: http://www.axolotl.com/Axweb.nsf/dflcb3e4a5eb7c9788256373007c67dd/5b856e3903a4b096882563c70058254c?Open Document.

Author unknown, "Elysium Presentation. Introduction to Reviewing Patient Results," Axolotl Corp., Jul. 24, 1997, 2 pgs.; available at: http://www.axolotl.com/Axweb.nsf/dflcb3e4a5eb7c9788256373007c67dd/4aa41155504ef4c3882563c700626717?OpenDocument.

Author unknown, "Elysium Presentation. Documents," Axolotl Corp., Jul. 24, 1997, 2 pgs.; available at: http://www.axolotl.com/Axweb.nsf/dflcb3e4a5eb7c9788256373007c67dd/a58e5e7d10a033c4882563c70067a1b2?OpenDocument.

Author unknown, "Elysium Presentation. Integrating Elysium into Your Office's Workflow," Axolotl Corp., Jul. 24, 1997, 1 pg.; available at: http://www.axolotl.com/Axweb.nsf/dflcb3e4a5eb7c9788256373007c67dd/7340abf7136a22df882563c800814204?OpenDocument.

Author unknown, "Elysium Presentation. The 'Action' Button," Axolotl Corp., Jul. 24, 1997, 1 pg.; available at: http://www.axolotl.com/Axweb.nsf/dflcb3e4a5eb7c9788256373007c67dd/048b748030549187882563c9006099b5?OpenDocument.

Author unknown, "Company Summary," MEDf/x Inc., 1998, pp. 1-12.

Author unknown, "Serveware™, What makes MEDf/x Serveware Practice Management Services so unique Inside and Outside . . . ," MEDf/x Inc., undated, 53 pgs.

Author unknown, "The Healthecare Information Partnership," CompuSense, Inc., undated, 6 pgs.

Author unknown, "Interface Engine," CompuSense, Inc., undated, 1 pg.

Author unknown, "C.S.I.nsight, The Semi-Annual Newsletter for MediSense Clients," CompuSense, Inc., Winter 1997, pp. 1-5.

Author unknown, "MediSense—Sophisticated LAN based management system for the rapidly changing healthcare industry.," CompuSense, Inc. Brochure, undated, 6 pgs.

Author unknown, "Management Services Organization Pamphlet-Information Request Form," CompuSense, Inc., Winter 1997, 2 pgs.

Author unknown, "Software designed to maximize today's computer power while embracing tomorrow's technology," CompuSense, Inc. Brochure, undated, 8 pgs.

Author unknown, "MediSense Reporting—Partial Set—Providing conclusive information for managing in the new business of medicine," CompuSense, Inc. Brochure, undated, 12 pgs.

Author unknown, "MediSense Reporting—Managed Care—Providing conclusive information for managing in the new business of medicine," CompuSense, Inc. Brochure, undated, 6 pgs.

Author unknown, "Client Profile," CompuSense, Inc. Brochure, undated, 15 pgs.

Author unknown, "AEQ Medical Information Manager, Patient Encounter Management," AEQ, 2 pgs.; available at: http://www.aeq.com/patenc.htm, (last visited Jul. 22, 1997).

Author unknown, "AEQ Medical Information Manager, Appointment and Resource Scheduling," AEQ, 1 pg.; available at: http://www.aeq.com/appoint.htm, (last visited Jul. 22, 1997).

Author unknown, "AEQ Medical Information Manager, Outcomes Research," AEQ, 2 pgs.; available at: http://www.aeq.com/outcomes.htm, (last visited Jul. 22, 1997).

Author unknown, "AEQ Medical Information Manager, Quality of Care Monitoring," AEQ, 2 pgs.; available at: http://www.aeq.com/quality.htm, (last visited Jul. 22, 1997).

Author unknown, "AEQ Medical Information Manager, Inventory Management," AEQ, 2 pgs.; available at: http://www.aeq.com/invent.htm, (last visited Jul. 22, 1997).

Author unknown, "AEQ Medical Information Manager, Administration," AEQ, 2 pgs.; available at: http://www.aeq.com/admin.htm, (last visited Jul. 22, 1997).

Author unknown, "AEQ Medical Information Manager, Billing Program," AEQ, 2 pgs.; available at: http://www.aeq.com/billing.htm, (last visited Jul. 22, 1997).

Author unknown, "AEQ Medical Information Manager, Share Administrative and Clinical Data Across your Network," AEQ, 1 pg.; available at: http://www.aeq.com/network.htm, (last visited Jul. 22, 1997).

Author unknown, "AEQ Medical Information Manager, Customization," AEQ, 1 pg.; available at: http://www.aeq.com/custom.htm, (last visited Jul. 22, 1997).

Author unknown, "AEQ Medical Information Manager, Integration," AEQ, 1 pg.; available at: http://www.aeq.com/integrat.htm, (last visited Jul. 22, 1997).

"AEQ Medical Information Manager," AEQ, undated, 9 pgs.

Author unknown, "AEQ I-Net, AEQ The High Speed Utility for HealthCare," AEQ, undated, 2 pgs.

Author unknown, "AEQ Medical Information Manager, The Right Information for the Right Decision," AEQ, undated, 2 pgs.

Author unknown, "AEQ Medical Information Manager, A Solid Return on Investment," AEQ, undated, 2 pgs.

Author unknown, "AEQ Medical Information Manager, Meeting Today's Challenges," AEQ, undated, 2 pgs.

Author unknown, "AEQ Launches Medical Information Manager at Windows on Health Care Conference," AEQ, Sep. 17, 1996, 3 pgs.

Author unknown, "Medi-Cal Computer Media Claims System, Remittance Advice Detail Manual," Operations Department, Electronic Data Systems Corporation, Jan. 1996, 131 pgs.

Author unknown, "Overview of SmartCare™," Vantage Point, Inc., undated, 4 pgs.

Author unknown, "VP-MED™ Features and Functions," Vantage Point, Inc., undated, 5 pgs.

Brady, "A Note from Vantage Point: IH-Med has been renamed SmartCare™," Dallas Business Journal, Aug. 19, 1996, 2 pgs.

Author unknown, "VP-MED™—the complete practice management system for multi-site groups," and "SmartCare™ the desktop resource utilization analysis and capitation forecasting system," Vantage Point, Inc., undated, 6 pgs.

Author unknown, "Technical Highlights of All Vantage Point Information Systems," Vantage Point, Inc. undated, 5 pgs.

Author unknown, "NextGen™ Free Yourself to Practice Medicine," Clinitec International, Inc. 1996, 9 pgs.

Author unknown, "MicroMed Technical Specifications and Architecture," undated, 4 pgs.

Author unknown, "Practice Management Solutions on the Windows NT Platform," Microsoft Healthcare, vol. 3, 2 pgs.

Author unknown, "Bayfront Medical Center," MicroMed Healthcare Information Systems, Inc., 1996, 1 pg.

Author unknown, "Bay Medical Center," MicroMed Healthcare Information Systems, Inc., 1996, 1 pg.

Author unknown, "Practice Management for the Enterprise," MicroMed Healthcare Information Systems, Inc., 1996, 4 pgs.

Author unknown, "PrincipalCare," MicroMed Healthcare Information Systems, Inc., 1996, 1 pg.

Author unknown, "Western Physician Data Services," MicroMed Healthcare Information Systems, Inc., 1996, 1 pg.

Author unknown, "Save Time. Save Lives. Save Money," STAT, undated, 6 pgs.

Author unknown, "STAT System Components," STAT, undated, 2 pgs.

Author unknown, "The STAT Service Advantage. What Makes STAT Different?" STAT, undated, 1 pgs.

Author unknown, "STAT Selected By Two Physicians' Groups. Specialists Move to Electronic Medical Records Systems," STAT, Sep. 12, 1997, 2 pgs.

Author unknown, "STAT Announces New Executives in Management Team," STAT, Sep. 19, 1997, 2 pgs.

Author unknown, "Logician®, Ambulatory EMR for the entire healthcare enterprise," MedicaLogic, 1996, 4 pgs.

Author unknown, "LinkLogic™, Integrating electronic medical records and systems of care," MedicaLogic, 1996, 4 pgs.

Author unknown, "PracticeLogic™, Clinical content for disease management and quality of care reporting," MedicaLogic, 1996, 4 pgs.

Author unknown, "AccessLogic™, Giving physicians access to complete information," MedicaLogic, 1996, 4 pgs.

Author unknown, "ScheduLogic™, Linking effective scheduling with electronic medical records," MedicaLogic, 1996, 2 pgs.

Author unknown, "SucessLogic™, Delivering successful EMR implementation through consulting, training, and support," MedicaLogic, 1996, 4 pgs.

Author unknown, "MedicaLogic Brochure", MedicaLogic, Inc., 1996, 18 pgs.

Author unknown, "Logician®, Ambulatory EMR for the entire healthcare enterprise," MedicaLogic, pp. 1-8; available at: http://www.medicalogic.com/products/logician.html, (last visited Jul. 22, 1997).

Author unknown, "ScheduLogic™, Linking effective scheduling with electronic medical records," MedicaLogic, pp. 1-2; available at: http://www.medicalogic.com/products/schedule.html, (last visited Jul. 22, 1997).

Author unknown, "LinkLogic, Seamless integration with other systems of care," MedicaLogic, pp. 1-4; available at: http://www.medicalogic.com/products/link.html, (ast visited Jul. 22, 1997).

Author unknown; "AccessLogic, Giving physicians access to complete information," MedicaLogic, pp. 1-4; available at: http://www.medicalogic.com/products/access.html, (last visited Jul. 22, 1997).

Author unknown, "PracticeLogic, Clinical content for disease management and quality of care reporting," MedicaLogic, pp. 1-3; available at: http://www.medicalogic.com/products/practice.html, (last visited Jul. 22, 1997).

Author unknown, "SucessLogic, Delivering successful EMR implementation through consulting, training and support," MedicaLogic, pp. 1-3; available at: http://www.medicalogic.com/products/success.html, (last visited Jul. 22, 1997).

Leavitt, "Office EMR: Three keys to physician acceptance," MedicaLogic, Inc., pp. 1-3; available at: http://www.medicalogic.com/press/articles/articlel.html, (last visited Jul. 22, 1997).

Author unknown, "A Return-on-Investment Analysis, Electronic Medical Records in the Outpatient Setting," MedicaLogic, 1996, pp. 1-25.

Author unknown, "Selecting an Electronic Medical Record: Measuring the Field," MedicaLogic, pp. 1-8; available at: http://www.medicalogic.com/press/articles/article3.html, (last visited Jul. 22, 1997).

Author unknown, "MedSys for Windows™. Let MedSys Manage Your Practice So You Can Practice Medicine!" InfoSys, Inc., undated, 11 pgs.

Author unknown, "ECLIPSE—Physician's Software for Windows," HNA Computer Systems, Inc., undated, 23 pgs.

Author unknown, "Navigating ECLIPSE for Windows," HNA Computer Systems, Inc., undated, 10 pgs.

Author unknown, "ECLIPSE™ Physicians Software—Information Packet," HNA Computer Systems, Inc., 1997, 15 pgs.

Author unknown, "Physicians Quality Care Chooses Reynolds' Integrated Practice Management System" Reynolds & Reynolds, Aug. 12, 1996, 2 pgs.

Gilbert, "Letter to ACOG Meeting Attendee," Avanta Medical Information Systems, Apr. 1997, 1 pg.

Author unknown, "Avanta News", Avanta Medical Information Systems Newsletter vol. 10, Issue 1, Jan. 1997, pp. 1-4.

Avanta Medical Information Systems, "Presenting Avanta Chart™ the new paradigm in Electronic Medical Records," undated, p. 1.

Author unknown, "Avanta Medical Information Systems Brochure," Medical Applications Corporation, 1997, 5 pgs.

Author unknown, "How many of these . . . " Brochure, CR Complete Business Systems, Inc., undated, 4 pgs.

Author unknown, "Tomorrow's software solutions . . . ," American Medical Management, Ltd., undated, 4 pgs.

Author unknown, "Quality Report Cards . . . ," American Medical Management, Ltd., undated, 1 pg.

McCall, "Millennium Medical Software, a Profile" Brochure, Millennium Medical Software, Inc., 1997, pp. 1-93.

Author unknown, "Prices, Training and Support for Millennium Medical Software," Millennium Medical Software, Inc., Nov. 1996, 3 pgs.

Author unknown, "MediMAX™ Overview," Healthcare Communications, Nov. 1996, pp. 1-8.

Author unknown, "Simplifying the Business of Health Care," Healtheon Corporation, 1996, 6 pgs.

Thompson, "Easier Said Than Done," Hospitals and Health Networks, Jul. 5, 1996, pp. 29-32.

Kohane, et al., "Building National Electronic Medical Record Systems via the World Wide Web," Journal of the American Medical Informatics Association, vol. 3, No. 3, May/Jun. 1996, pp. 191-205.

Kohane, "Exploring the Functions of World Wide Web-Based Electronic Medical Record Systems," Medical Resources on the Net, vol. 13, No. 4, 1996, pp. 339-345.

Author unknown, "Fall 1998 Healthcare Guide to the Internet," COR Healthcare Resources, vol. 3, Fall 1998, pp. 32-33 and pp. 53-54.

Author unknown, "Spring 1998 Healthcare Guide to the Internet," COR Healthcare Resources, vol. 1, 1998, pp. 13, 31.

Author unknown, "Overview and Features," ValueMed Systems, undated, 4 pgs.

Author unknown, "The Utilization Module," ValueMed Systems, undated, 2 pgs.

Author unknown, "The Costs Module," ValueMed Systems, undated, 2 pgs.

Author unknown, "ValuMed—The Enrollment Module," ValueMed Systems, undated, 2 pgs.

Author unknown, "The Modeling Module," ValueMed Systems, undated, 2 pgs.

Author unknown, "Your Guide to Electronic Transactions on HealthWire®-Direct," Blue Cross/Blue Shield of Massachusetts, Summer 1999, pp. 1-29.

Author unknown, "WebMD Practice$^{SM}$, An Overview," Healtheon WebMD, 1999, 4 pgs.

Author unknown, "The World's First End-to-End Internet Healthcare Solution," Healtheon WebMD, 1999, 6 pgs.

Bordow, "Charting a New Course," Physicians and Computers, May 1993, 4 pgs.

Cislowski, "Saving money and pleasing patients at the same time," Medical Economics, Sep. 25, 1995, pp. 151-160.

Health Quality, "About Health Quality," undated, 5 pgs.

Author unknown, "Medical information comes of age. A new generation of healthcare tools is here," Azron® Incorporated, undated, 4 pgs.

Author unknown, "Azron® EMR—Electronic Medical Records Proven Today, the Vision for Tomorrow," Azron® Incorporated, 1997, 4 pgs.

Ralston, "Paperless Made Simple," Physicians and Computers, vol. 14, No. 3, Nov. 1996, 4 pgs.

Author unknown, "Visions in Healthcare" Wireless vol. 5, No. 5, Wireless Publishing Co., May 1996, 2 pgs.

Hagland, "Outpatient clinics without the paperwork," Health Management Technology, May 1997, 6 pgs.

Author unknown, "Giving a Clinic on Automating Records," Health Data Management, vol. 4, No. 7, Jul. 1996, 4 pgs.

Ralston, "Paperless Charts: The Future of Medical Records, Information Management Technology in Health Care," Cost & Quality, Quarterly Journal, vol. 2, No. 4, Oct. 1996, pp. 13-16.

Author unknown, "MarketScan$^{SM}$, Database Fields," MEDSTAT Systems, Inc. 1992, 2 pgs.

Author unknown, "The MEDSTAT Group," MEDSTAT Systems, Inc., Aug. 1994, 4 pgs.

Electronic Healthcare Systems, Inc., "careREVOLUTION—Leading the Revolution in Healthcare Information," undated, 15 pgs.

Andrew et al., "Critical Questions to be Answered During CPR System Procurements," Lanier Healthcare 1996 Annual HIMSS Conference & Exhibition, Mar. 4, 1996, pp. 1-5.

Andrew et al., "The Computer-Based Patient Record: An Essential Technology for Health Care," Healthcare Informatics, May 1997, pp. 38-59.

* cited by examiner

FIG. 4

Patient Registration

- Last Name
- First Name & M. Initial
- Sex
- Prev Last Name
- DOB
- SSN
- Address
- Zip
- City
- State
- Home Phone
- Work Phone
- Email
- Usual Provider
- ID Number Override
- General Hospital Med. Record
- How did you hear about us ?
- Specify (If other, above)
- Private Notes
- Other Notes

- Date of Registration
- Dept of Registration
- Primary Department
- Marital Status
- Languages
- Ethnicity

*guarantor (name to whom statements are sent)*
- Guarantor Last Name
- Guarantor First Name + M. Initial

*guardian is the patient's legal guardian*
- Guardian Last Name
- Guardian First Name + M. Initial

*other patient contact info*
- Emergency Contact Name
- Emergency Contact Relation
- Emergency Contact Phone
- Employer Name
- Employer Phone

404

408

General

Save | Save and Add Insurance | Save and Schedule

Check In                                                                                  Check In 504 — action bar  click the bar to edit registration info, schedule the patient, print label, etc.
     ☑ view/cancel today's appointments
     Reason for Cancellation [ ▾ ]              [ Cancel Checked Appointment(s) ]

508 — edit appointment information
     Appt Type    [ ▾ ]          Dept [ ▾ ]           Rendering Provider [ ▾ ]
     Notes/Reason  add note
     Prior Auth #

512 — insurance
     primary  new primary insurance

516 — verify & edit registration information
     Patient Notes                                                              [ ◀ ▶ ]

Patient Outstanding  $0.00   view billing summary
     Last Name                                Status           [ ▾ ]
     First Name & M. Initial                  Sex              [ ▾ ]
     Prev Last Name                           Home Phone
     DOB            ◈                         Work Phone
     SSN                                      Primary
     Address                                  Department       [ ▾ ]
     Zip                                      Usual Provider   [ ▾ ]
     City                                     Marital Status   [ ▾ ]
     State                                    Ethnicity        [ ▾ ]
     Email                                    General Hospital
                                              Med. Record

[ Save registration changes ]

520 — Collect Patient Payment
     Post Date                       ◈
     Time of Service Batch                    [ ▾ ]
     Method
     Check or CC Number Service Date:              Procedure                       Outstanding Amount
     Today's Copay (expected office visit copay) $ (    )                            Today's Payment
     Coinsurance (usual coinsurance      %)                                          $

PRACTICE MANAGEMENT AND BILLING AUTOMATION SYSTEM

RELATED APPLICATIONS

This application claims priority to U.S. provisional patent application, Ser. No. 60/223,235, filed on Aug. 4, 2000, and entitled "Practice Management and Billing Automation System," the entire disclosure of which is hereby incorporated by reference.

FIELD OF THE INVENTION

The invention relates generally to the management of medical practices and more particularly to a medical practice management and billing automation system.

BACKGROUND OF THE INVENTION

High administrative costs for filing and processing health insurance claims have typically been the bane of the health insurance industry for decades. Insurance claims include various information associated with a patient, such as the patient's insurance eligibility for a particular medical procedure. An unfortunate reality of today's healthcare industry typically is that billions of dollars are wasted in the processing of flawed insurance claims. Additionally, the processing of these insurance claims often wastes valuable time, typically resulting in an average revenue recognition cycle of over seventy days.

As a specific example, a medical professional (e.g., a receptionist) can verify the insurance eligibility of a patient by calling the particular insurance company. Alternatively, the receptionist can request eligibility information for the patient using a web portal electronically connected to the insurance company's web page. The receptionist types information about the patient into the web portal, transmits the information to the insurance company's web server, retrieves a response, and manually enters this information into a computer of the medical practice. Due to the large number of steps involved for this task and also due to the heavy workload frequently placed on the professionals performing these tasks, data entry errors often occur. These errors typically slow the process of successfully submitting an acceptable claim to the insurance company. For instance, the medical professional (e.g., receptionist) can forget to initiate an eligibility check, which can lead to significant billing and claim processing problems.

Other areas associated with the management of a medical practice, such as the claim acknowledgement area, often experience the same or similar problems. Particularly, once a medical practice submits an insurance claim to the insurance company, a medical professional typically has to sift through numerous claim acknowledgement reports to determine if the claim has reached its correct destination. This is a time-intensive, manual process that can be inundated with human error. These errors include, for example, errors in the comparison of the content of a report to the claim submission records stored in a medical practice management system. Another aspect of the process that often has similar problems includes the process of checking on the status of the claim as the claim traverses the insurance company system.

Given the extent of wasted time and money associated with the process, there exists a need to manage a medical practice in a more efficient manner and provide insurance claims with fewer or no errors.

SUMMARY OF THE INVENTION

The present invention automatically and repeatedly interacts with an insurance company system and/or applies rules to efficiently manage a medical practice and provide insurance claims with a reduced number of errors. In one aspect, the invention includes a method for managing a medical practice. The method includes communicating with a medical practice client user interface over a first communications network and a payor server over a second communications network. The method also includes receiving information associated with an event related to a patient from the medical practice client user interface and/or the payor server and performing one or more tasks associated with the event. Additionally, the information associated with the event is used to create an insurance claim following completion of the task(s). The invention also automatically and repeatedly interacts with the information associated with the event in connection with the performed tasks by applying one or more rules in a set of rules and/or performing transactions with the payor server.

In one embodiment, the method includes the step of verifying the information before, during, and/or following performing the task(s) associated with the event. The method can also include receiving an error notification and performing a correcting action, which can include transmitting an error message denoting an error to the medical practice.

In another aspect, the invention includes a medical practice management system. The medical practice management system includes a medical practice client user interface, a payor server, and a medical practice management server computer. The medical practice client user interface communicates with a patient and the payor server communicates with a payor organization. The medical practice management server computer receives information associated with an event related to a patient from the medical practice client user interface and/or the payor server. The medical practice management server additionally includes a workflow processing engine, a rules engine, and an intelligent transactions relationship module.

The workflow processing engine performs one or more tasks associated with the event and the rules engine repeatedly and automatically interacts with the information associated with the event by applying one or more rules in a set of rules to the information in connection with one or more of the tasks. The intelligent transactions relationship module repeatedly and automatically interacts with the information associated with the event by performing transactions with the payor server in connection with the performance of one or more tasks.

In one embodiment, the workflow processing engine further comprises a verifier to verify the information before, during, and/or after performing the tasks associated with the event.

BRIEF DESCRIPTION OF THE DRAWINGS

The above and further advantages of this invention may be better understood by referring to the following description in conjunction with the accompanying drawings. The drawings are not necessarily to scale, emphasis instead being placed upon illustrating the principles of the invention.

FIG. 4 illustrates an exemplary embodiment of a patient registration screen according to the present invention.

FIG. 5 illustrates an exemplary embodiment of a patient check-in screen according to the present invention.

FIG. 7A illustrates an exemplary embodiment of a claim entry screen according to the present invention.

FIG. 7B illustrates an exemplary embodiment of an advanced claim entry screen according to the present invention.

FIG. 7C illustrates an exemplary embodiment of a claim review screen according to the present invention.

FIG. 7D illustrates an exemplary embodiment of a claim edit screen according to the present invention.

FIG. 7E illustrates an exemplary embodiment of an explanation portion of the claim edit screen shown in FIG. 7D according to the present invention.

DETAILED DESCRIPTION

Figure 1:
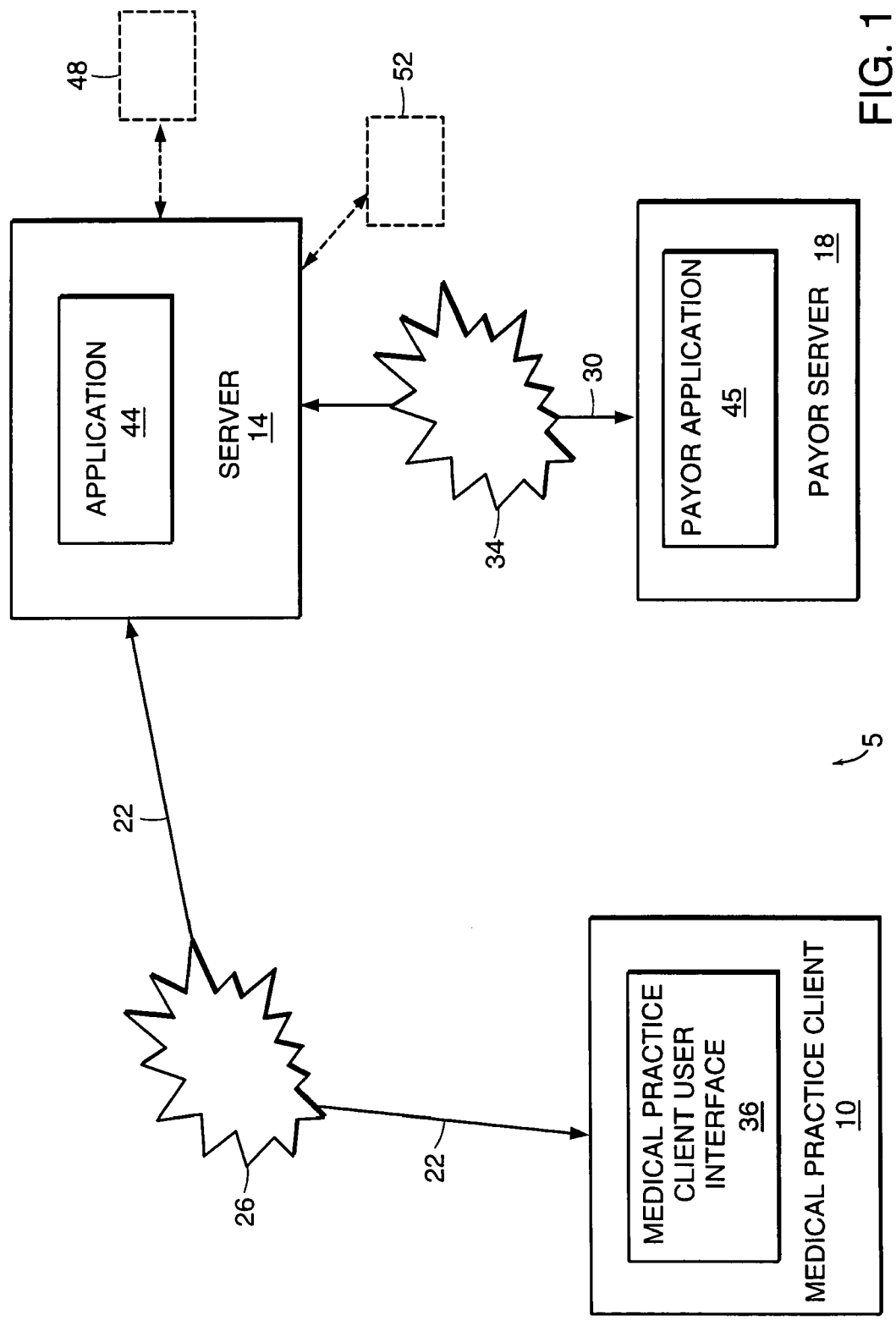
FIG. 1 illustrates a block diagram of an embodiment of a medical practice management system according to the present invention.

FIG. 1 illustrates a block diagram of an embodiment of a medical practice management system 5 that includes a medical practice client computer (or medical practice client) 10, a medical practice management server (or server) 14, and a payor server computer (or payor server) 18. The medical practice client 10 is in communication with the medical practice management server 14 over a medical practice client-server communication path 22 and passes through a first communications network (or medical practice client-server network) 26. The medical practice management server 14 is also in communication with the payor server 18 over a payor server communication path 30 and passes through a second communications network (or payor server network) 34. It should be noted that FIG. 1 is an exemplary embodiment intended only to illustrate, and not limit, the invention.

The medical practice client-server network 26 and the payor server network 34 can be a local-area network (LAN), a medium-area network (MAN), or a wide area network (WAN) such as the Internet or the World Wide Web (i.e., web). In one embodiment, the medical practice client-server network 26 (e.g., the medical practice client-server communication path 22) supports secure communications. In a further embodiment, communications occur after a medical care provider's, or user's, password is verified by the medical practice management server 14. Exemplary embodiments of the communication paths 22, 30 include standard telephone lines, LAN or WAN links (e.g., T1, T3, 56 kb, X25), broadband connections (ISDN, Frame Relay, ATM), and wireless connections. The connections over the communication paths 22, 30 can be established using a variety of communication protocols (e.g., TCP/IP, IPX, SPX, NetBIOS, Ethernet, RS232, and direct asynchronous connections).

The medical practice client 10 can be any personal computer (e.g., 286, 386, 486, Pentium, Pentium II, Macintosh computer), Windows-based terminal, network computer, wireless device, information appliance, RISC Power PC, X-device, workstation, mini computer, main frame computer, personal digital assistant, or other computing device that has a windows-based desktop, can connect to a network and has sufficient persistent storage for executing a small, display presentation program. Windows-oriented platforms supported by the medical practice client 10 can include, without limitation, WINDOWS 3.x, WINDOWS 95, WINDOWS 98, WINDOWS NT 3.51, WINDOWS NT 4.0, WINDOWS 2000, WINDOWS CE, MAC/OS, Java, and UNIX. The medical practice client 10 can include a visual display device (e.g., a computer monitor), a data entry device (e.g., a keyboard), persistent or volatile storage (e.g., computer memory) for storing downloaded application programs, a processor, and a mouse.

The medical practice client 10 includes a medical practice client user interface 36. The interfaces 36, 40 can be text driven (e.g., DOS) or graphically driven (e.g., Windows). In one embodiment, the medical practice client user interface 36 is a web browser, such as Internet Explor™ developed by Microsoft Corporation (Redmond, Wash.), to connect to the medical practice client-server network 26. In a further embodiment, the web browser uses the existing Secure Socket Layer (SSL) support, developed by Netscape Corporation, (Mountain View, Calif.) to establish the medical practice client-server network 26 as a secure network.

The medical practice management server 14 and the payor server 18 can be any personal computer described above. In one embodiment, the medical practice management server 14 hosts one or more applications 44 that the medical practice client 10 can access. Moreover, the payor server 14 can host one or more applications 45 that the medical practice management server 14 can access. In another embodiment, the medical practice management server 14 (and/or the payor server 18) is a member of a server farm, which is a logical group of one or more servers that are administered as a single entity. In the embodiment shown, the server farm includes the server 14, a second server 48, and a third server 52.

In a further embodiment, a second medical payor server computer (not shown) communicates with the server 14 through the payor server network 34.

In one embodiment, a medical care provider uses the medical practice client 10. Examples of the medical care provider include, but are not limited to, medical physicians, medically trained individuals, medical specialists, medical experts, receptionists, and the like. The medical practice client 10 is typically located in a medical practice. In one embodiment, the medical practice is the office of the medical care provider (e.g., a doctor's office), a hospital, other facilities providing medical treatment, and the like. Further, in one embodiment, a payor organization, or payor, uses the payor server 18. Although also referred to below as an insurance company, example embodiments of a payor organization also include, but are not limited to, health maintenance organizations (HMOs). More specifically, examples of payor organizations include, without limitation, Century Health and Benefits, HMO Blue, Harvard Pilgrim Health Care, MassHealth, Medicare, Neighborhood Health Plan, Tufts Associated Health Plan, United Healthcare, and the like.

Figure 2A:
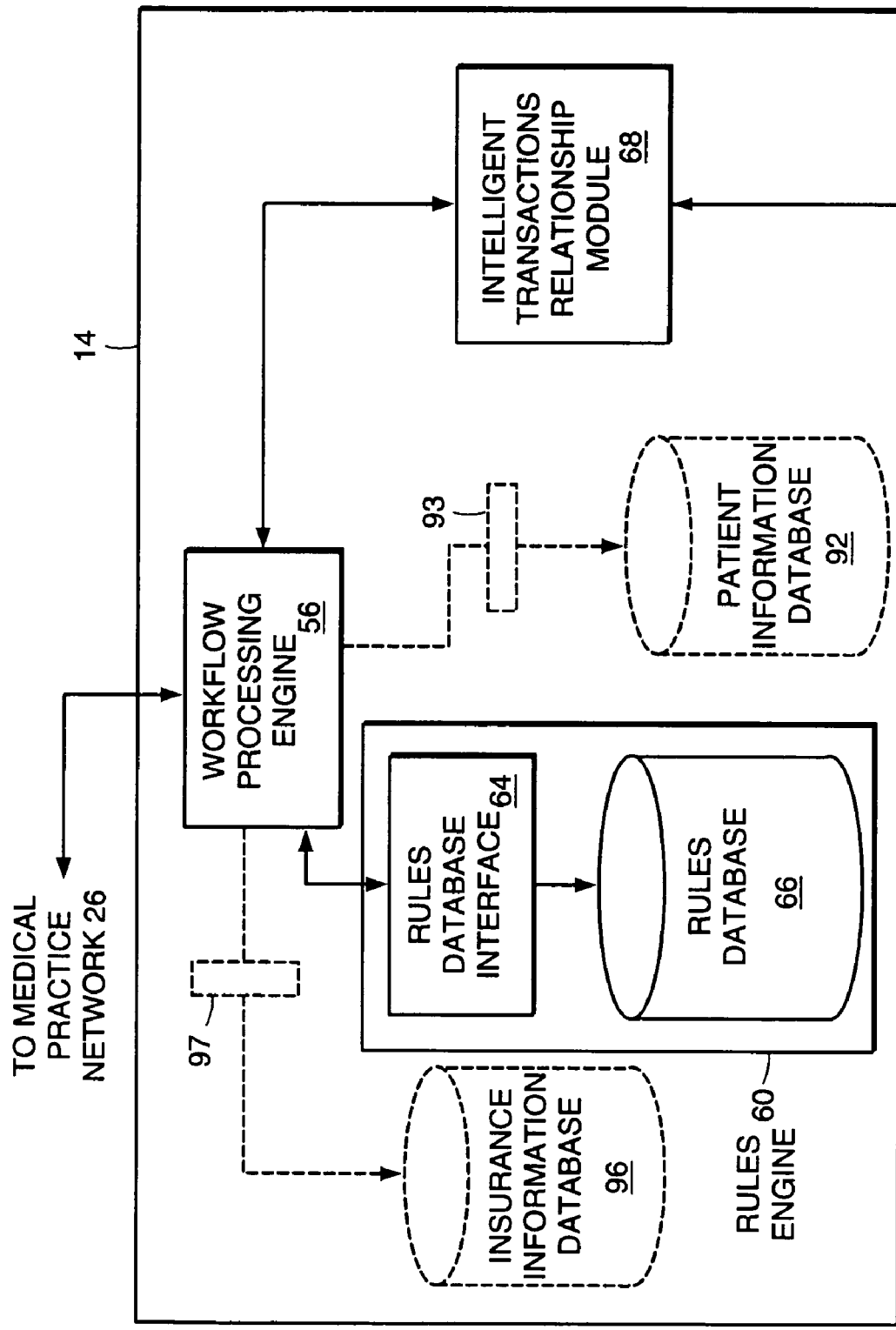
FIG. 2A illustrates a more detailed block diagram of an embodiment of a medical practice management server of the medical practice management system according to the present invention.

Referring to FIG. 2A, the medical practice management server 14 includes a workflow processing engine 56, a rules engine 60, and an intelligent transactions relationship (ITR) module 68. In one embodiment, the rules engine 60 includes a rules database interface 64 and a rules database 66. In one embodiment, the engines 56, 60 and/or the ITR module 68 are software modules located within the medical practice management server 14. In another embodiment, one or more of the engines 56, 60 and/or the ITR module 68 are externally located from the server 14 and communicate with the server 14.

In one embodiment, the workflow processing engine 56 is a software application that controls and manages the features and functions of the medical practice management system 5. The workflow processing engine 56 and the medical practice client 10 communicate over the medical practice client-server network 26. In operation, the medical practice client 10 transmits a medical care provider request containing information to the medical practice management server 14 using, for example, a common gateway interface (CGI) request. For example, when registering a new patient, a medical care provider operating the medical practice client 10 enters the relevant patient information on a patient registration template that the workflow processing engine 56 delivered to the medical practice client user interface 36.

The workflow processing engine 56 also checks the structure and composition of information entered by a medical care provider at the medical practice client 10 to ensure that the information is correct (i.e., structure and/or composition). Examples of information entered by a medical care provider at the medical practice client 10 include the patient's address, phone number, medical history, insurance information, diagnosis and procedure codes, and the like.

The workflow processing engine 56 is additionally in communication with the rules engine 60. The rules engine 60 enables real-time application of "rules" stored in the rules database 66. Described in more detail below with respect to FIG. 2B, a rule is coded logic that evaluates data and then performs an action.

The rules engine 60 can access and update information stored in the rules database 66 using the rules database interface 64. Although not shown in FIG. 2A, in another embodiment the rules database interface 64 is a software layer internal to the workflow processing engine 56. The rules database interface 64 can be, for example, an application program interface or a Component Object Model (COM) object, which was developed by Microsoft Corporation.

The rules database 66 and/or the rules database interface 64 may be written in a structured query language, such as SQL, developed by IBM Corporation (Armonk, N.Y.). In one embodiment, the rules database interface 64 uses a Lightweight Directory Access Protocol (LDAP) to access information in the rules database 66. Additionally, the rules database 66 can be external to the server 14 or may be internally situated in the server 14.

The rules database 66 includes insurance company rules that define the appropriate format and content of clinical and claim information that the payor server 18 processes. In one embodiment, the rules are subdivided into various classes. For example, the rules are divided into rules that have universal applicability to all claims for a specified payor, rules that apply only to one or more specific insurance packages from among the variety of insurance packages that the payor offers to medical care providers, and rules that apply only to specific medical care providers who provide care under one or more specific insurance packages.

Typically, a trigger invokes the application of a particular rule. For example, the submission of an insurance claim for a first payor could invoke the rules engine 60 to apply particular formatting rules associated with the first payor to format the claim to the first payor's specification.

To ensure that the rules database 66 contains current rules, the rules database 66 is frequently updated. In one embodiment, individual payors transmit rule updates/creations to the medical practice management server 14 via their payor server 18. Rule specialists review the rules transmitted by the payor server 18 and subsequently update the rules database 66. In one embodiment, the rules specialist performs any and all updates to the rules database 66. Alternatively, the updating of the rules database 66 can be automated upon receipt of a rule transmission from the payor server 18 or the medical practice client 18.

Additionally, a medical care provider can submit information to the medical practice management server 14 for subsequent update of the rules database 66 based on the medical care provider's experience with one or more payors. In yet another embodiment, the rules database 66 is updated with the server's historical analysis of previously submitted claims, especially those that were denied, to identify the reasons for denial. The historical analysis of previously submitted claims can facilitate the development of new rules for the rules database 66.

Figure 2B:
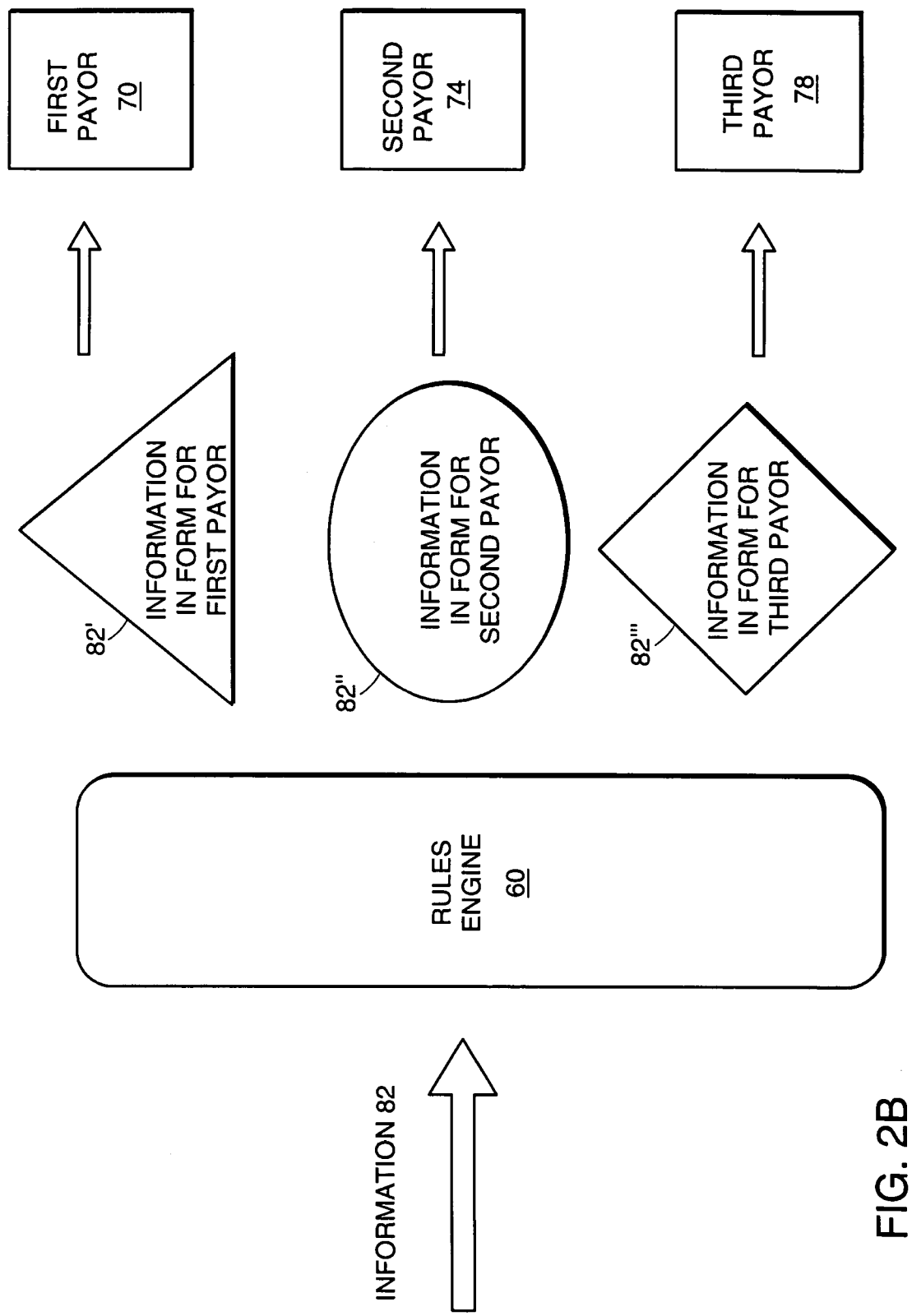
FIG. 2B illustrates a block diagram of an embodiment of the functions performed by a rules engine according to the present invention.

Referring to FIG. 2B, the rules engine 60 may interact with several payors (and therefore several payor servers 18), such as a first payor 70, a second payor 74, and a third payor 78. The rules engine 60 receives information 82, such as an insurance claim, from the workflow processing engine 56. In one embodiment, the rules engine 60 determines the payor 70, 74, 78 that the information 82 will be submitted by, for instance, searching the information 82 for a payor field. Once the rules engine 60 determines the receiving payor 70, 74, 78, the rules engine 60 applies the appropriate rules that are stored in the rules database 66 for the particular payor 70, 74, 78 to the information 82.

For example, the rules engine 60 applies the rules to the information 82 for the first payor 70 and subsequently transforms the originally received information 82 into first information 82' having a form acceptable to the first payor 70. Likewise, the rules engine 60 applies the rules to the information 82 for the second payor 74 and subsequently transforms the originally received information 82 into second information 82" having a form acceptable to the second payor 74. The rules engine 60 performs the same process to the information 82 to format the information 82 into third information 82''' acceptable to the third payor 78.

Referring again to FIG. 2A, in one embodiment the medical practice management server 14 also includes a patient information database 92 (shown in shadow) and an insurance information database 96 (shown in shadow). The workflow processing engine 56 stores all of the information associated with a registered patient in the patient information database 92. The patient information database 92 stores information associated with existing patients of the medical practice. This information can include the patient's address, phone number, zip code, height, weight, allergies, previous doctor(s), and the like. In one embodiment, the medical practice management server 14 indexes the patient information stored in the patient information database 92 by the patient name. In another embodiment, the server 14 indexes the patient information stored in the patient information database 92 with a patient identifier. The patient identifier can be a random number, a predetermined integer (such as a patient counter), the patient's zip code, the patient's phone number, and the like. The workflow processing engine 56 typically accesses the patient information database 92 using a patient information database interface 93.

Similarly, the workflow processing engine 56 can store all of the information associated with an insurance company in the insurance information database 96, such as the insurance company's address, the amount of insurance coverage for a particular patient, and the like. Moreover, the workflow processing engine 56 can access the insurance information database 96 using an insurance information database interface 97.

In operation, as the workflow processing engine 56 receives information from the medical practice client 10, the workflow processing engine 56 determines on a real time basis whether all of the required information has been provided and whether the information is in the correct format. In the event that there is a deficiency in the information, the workflow processing engine 56 alerts the medical care provider (e.g., receptionist), or user, for additional information. Alternatively, the workflow processing engine 56 corrects the defect.

For instance, if the rules engine 60 contains a rule about member identification formatting for a particular payor, the rules engine 60 determines the rule in the rules database 66 and communicates the information to the workflow processing engine 56. The workflow processing engine 56 communicates this information to the medical practice client 10 when a medical care provider (e.g., receptionist) is registering a patient. If the medical care provider (e.g., receptionist) errs, the medical practice management server 14 alerts the medical care provider (e.g., with a warning message) to correct the error. This enables medical care providers to generate claims with no errors (i.e., referred to below as clean claims) for the mutual benefit of the medical care provider and the payor. Additionally, the medical care providers can obtain the information associated with an alert while the patient is physically present.

The workflow processing engine 56 is also in communication with the ITR module 68. The ITR module 68 executes transactions sent to and received from the payor server 18. Thus, the majority of provider/payor transactions can be accomplished electronically, with little or no human intervention. Examples of these transactions include, without limitation, claim submittals, claim receipt acknowledgements, claim status checks, patient eligibility determinations, authorization and referral requests and grants, and remittance advice. For example, a predetermined number of days before a scheduled patient visit, the ITR module 68 automatically checks patient eligibility with the applicable payor identified during the patient registration process. After a patient visit and the completion of the claim template, the claim is submitted to the payor server 18 via the ITR module 68.

In one embodiment, upon receipt of an insurance claim, the payor client 18 transmits a confirmation back to the medical practice management server 14. Later, on a schedule determined by the medical care provider, the ITR module 68 checks the claim status and notifies the medical practice client 10 accordingly. After the ITR module 68 analyzes the claim and generates remittance advice, the ITR module 68 parses the electronic payment and allocates the payment among the individual charge line items for the services provided. Once the medical care provider approves the allocations, the payments are posted to the provider's accounts.

Although described above as individual components, the engines 56, 60 and the ITR module 68 can be combined into one component or any number of components. Similarly, the databases, 66, 92, 96 could also be combined into one database and can be external or internal to the server. In other embodiments, the patient information and/or the insurance information is stored on a disk, such as a compact disk or a ZipDrive, developed by Iomega Corporation (Roy, Utah).

The medical practice management system 5 performs operations in response to an event related to a patient. Although a patient visit is used hereinafter as the event, the event can also be an emergency phone call to the medical provider, an emergency visit to the medical provider, a "virtual" visit to the medical practice client 10 (i.e., on-line communications with the medical practice client 10, such as over the Internet), and the like.

The medical practice management server 14 receives information associated with the event related to a patient from the medical practice client 10 and/or from the payor server 18 over the respective network 26, 34. The medical practice management server 14 performs one or more tasks associated with the event and then uses the information associated with the event to create an insurance claim after the completion of the task(s). An example of the information associated with the event is the patient information. The medical practice management server 14 automatically and repeatedly interacts with the information associated with the event in connection with the performed tasks by applying one or more rules in a set of rules and/or by performing transactions with the payor server 18.

Figure 3A:
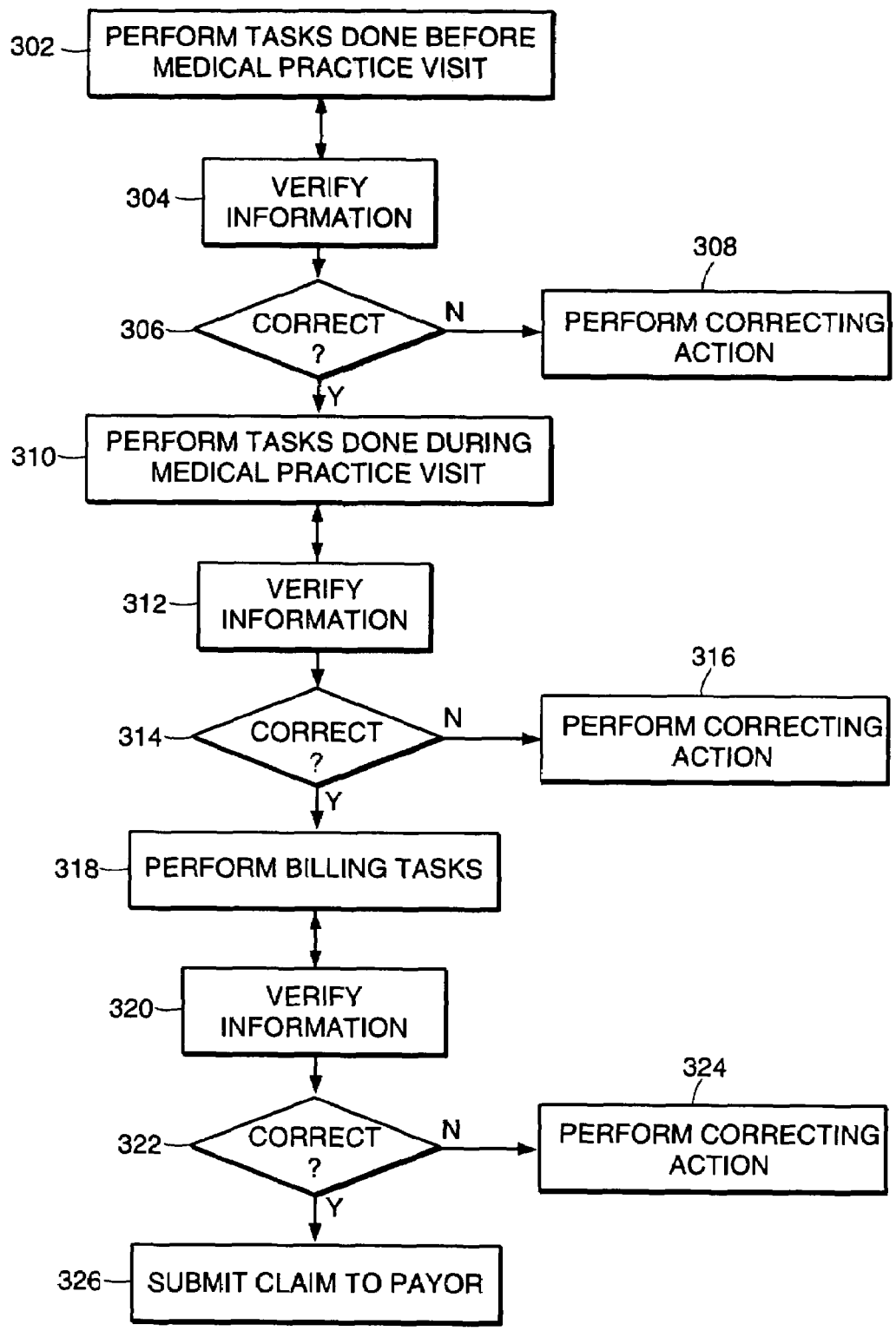
FIG. 3A illustrates a flow diagram of an embodiment of the steps performed by the medical practice management system according to the present invention.

Referring to FIG. 3A, the workflow of the medical practice management system 5 can typically be broken down into two sub-categories: 1) the patient workflow and 2) the billing workflow. The patient workflow can be sub-divided into tasks performed by the medical practice management system 5 before the patient visit to the medical practice and tasks performed by the medical practice management system 5 during the patient visit to the medical practice.

The medical practice management server 14 performs particular tasks before the patient visits the medical practice (step 302). In one embodiment, at the end of each task within the group of tasks that the medical practice management server 14 performs before the patient visit, the medical practice management server 14 automatically verifies, or interacts with, all information related to the task that the medical practice management server 14 receives from the medical practice client 10 (step 304). In another embodiment, the medical practice management server 14 automatically verifies all information related to the task (step 304) in real-time (i.e., substantially simultaneous with the medical care provider entering the information into the medical practice client 10). The medical practice management server 14 automatically interacts with/verifies the information by applying a particular rule (i.e., stored in the rules database 66) and/or by communicating with the payor server 18 (via the ITR module 68). The type of interaction/verification that occurs can also depend on the type of information. Additionally, the interaction/verification with the information can include a separate workflow that involves multiple steps and processes. In particular, the interaction/verification may also include application of a set of rules, communication with a payor organization via the ITR module 68, checking the format of the information, and the like at any time (e.g., before, during, after) throughout one or more of the performed tasks.

For example, if the medical practice client 10 transmits a form that includes the patient's address and zip code, and the zip code entered into the form has six digits instead of five, the medical practice management server 14 (i.e., the workflow processing engine 56) determines that the zip code is incorrect (step 306) and subsequently performs a correcting action on the zip code (step 308). In one embodiment, the workflow processing engine 56 alerts the medical care provider that the zip code is incorrect. In a further embodiment, the workflow processing engine 56 alerts the medical care provider with a pop-up window on the user interface 36 of the medical practice client 10. In yet another embodiment, the workflow processing engine 56 alerts the medical care provider with a voice message stating that the zip code is incorrectly entered.

Although described above and below as alerting the medical provider via the medical practice client 10, the correcting action could be any step to help correct the problem. For example, the workflow processing engine 56 could highlight the error(s) on the screen in a predetermined color, such as yellow. In yet another embodiment, the workflow processing engine 56 automatically corrects the zip code. For instance, the workflow processing engine 56 uses the patient's name to search the patient information database 92 for the patient's zip code stored in the database 92. Additionally, the correcting action can be performed by the workflow processing engine 56, the rules engine 60, and/or the ITR module 68. Moreover, the correcting action can be performed with operator assistance, such as with the assistance of a rules specialist.

After completing the tasks associated with the patient before visiting the medical practice, the medical practice management server 14 begins performing tasks associated with the patient's visit to the medical practice at the start of the patient's visit (step 310). The workflow processing engine 56 automatically verifies and checks the entered information during/after the performance of each task (step 312). If the medical practice management server 14 determines an incorrect/inaccurate piece of data, the workflow processing engine 56 alerts the medical care provider of the inaccuracy (step 316). Following the patient's visit to the medical practice, the medical practice management server 14 performs the billing tasks associated with the services provided to the patient (step 318). As shown in steps 320-324, the workflow processing engine 56 automatically verifies the billing information and alerts the medical care provider if necessary. It should be noted that, at each stage of the process (e.g., tasks performed before the visit to the medical practice, tasks performed during the visit to the medical practice, tasks performed during the billing process), the medical practice management server 14 verifies and checks each piece of information entered without human intervention (e.g., the medical provider). The verification and checking can be through rule application or by communication with a payor server 10 (via the ITR module 68). This can be done prior to the submission of an insurance claim to enable later submissions of more accurate claims (e.g., flawless claims) to the payor (step 326). Alternatively, this can be done during or following claim submission to the payor server 18.

Further, although described as a linear flow of operations, the steps illustrated in the FIGS. 3A-3F can be performed at various times before, during, or after the performed tasks. The steps illustrated can also be performed simultaneously. Moreover, the information received in one particular step can be used in other steps in the same workflow or other steps in other workflows. For example, the medical practice management server 14 (i.e., one or more of its components 56, 60, 68) can retrieve information associated with a patient at any of the steps illustrated in any of the FIGS. 3A-3F and can repeatedly use the information again at any/all other steps throughout any/all of the workflows. Thus, the use of the information received at one particular step is dependent upon the location within a workflow as well as the information being accessed and/or entered into the medical practice client 10 and/or the medical practice management server 14 and/or the payor server 18. Consequently, FIGS. 3A-3F are intended only to illustrate, and not limit, the invention.

The workflow processing engine 56 receives a request for an appointment from the medical practice client 10 with respect to a particular patient (step 328). In one embodiment, the medical practice client 10 transmits the name of the individual to the medical practice management server 14 to determine whether the individual is an established patient or a new patient. The workflow processing engine 56 searches for the patient in the patient information database 92 (step 330) using the index of the patient information database 92 or a portion of the indexing field to determine if the patient is an established patient (step 332). For instance, the workflow processing engine 56 can search for the patient in the patient information database 92 using the patient's full name or a portion of the patient's name (e.g. last name).

If the workflow processing engine 56 does not find patient information associated with the patient in the patient information database 92, then the patient is a new patient. In one embodiment, the workflow processing engine 56 then transmits a message to the medical practice client 10 to request registration information from the medical practice client 10. In a further embodiment, the workflow processing engine 56 transmits a registration screen to the medical practice client 10 in which the medical care provider (e.g., receptionist) enters patient information associated with the patient into the medical practice client 10. An example of a registration screen 400 is illustrated in FIG. 4 and is described in more detail below.

The medical care provider (e.g., receptionist) enters the patient information associated with the patient into the medical practice client 10 and the medical practice client 10 transmits the patient information to the medical practice management server 14. The work flow processing engine 56 receives the patient information (step 334) and automatically verifies/checks the format and accuracy of the information entered at the medical practice client 10 (step 336). If the information has an incorrect format or is inaccurate (step 338), the workflow processing engine 56 can alert the medical care provider of the inaccuracy (step 340).

Before a patient's visit to the medical practice, the medical care provider also collects insurance information from the patient. The medical care provider client 10 transmits the information to the medical practice management server 14. The workflow processing engine 56 receives the insurance information associated with the patient (step 342) and automatically verifies the insurance eligibility of the patient (step 336). In one embodiment, the ITR module 68 verifies the insurance eligibility by communicating with the payor server 18 via the payor server network 34.

Figure 3B:
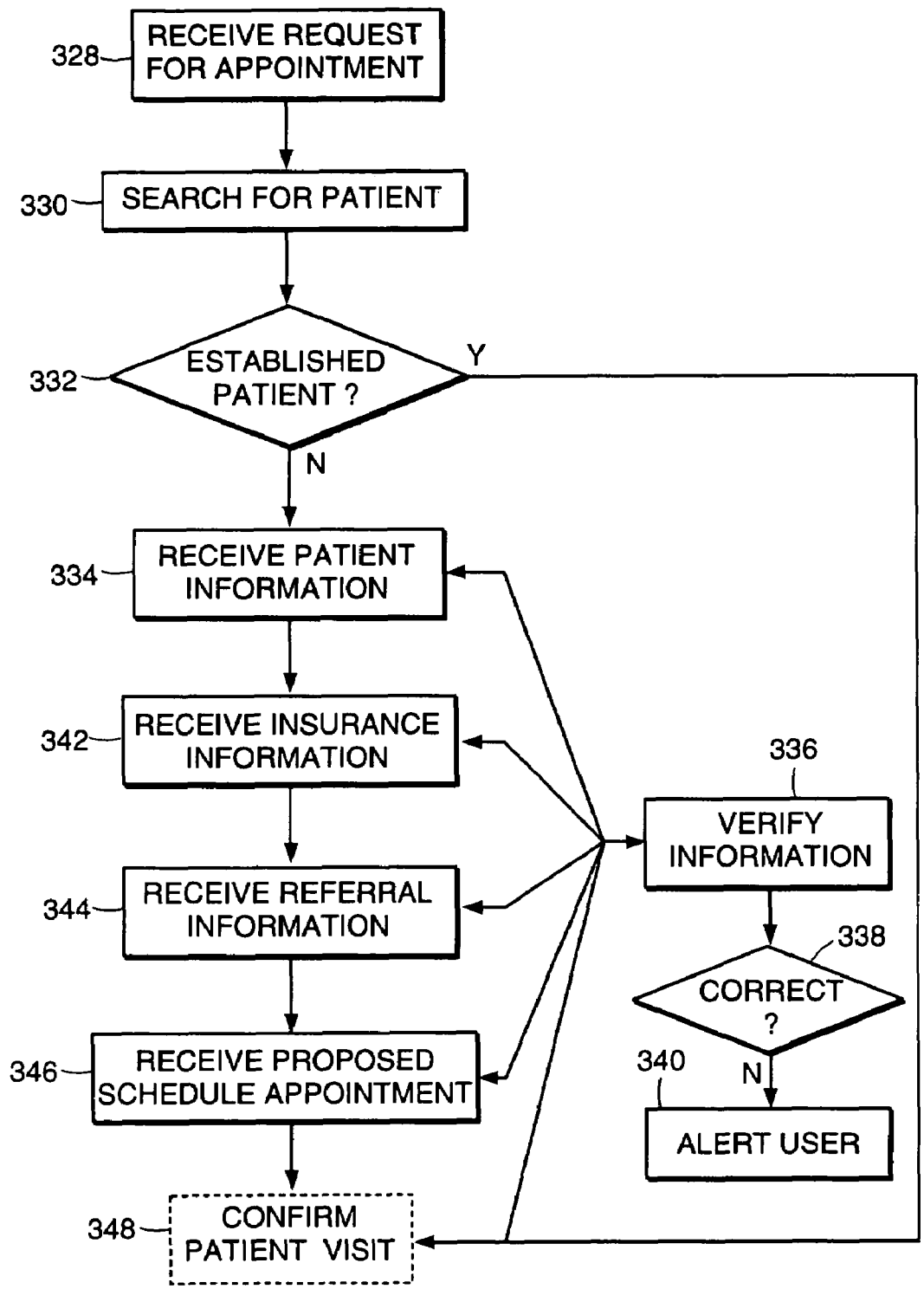
FIG. 3B illustrates an embodiment of a patient workflow diagram performed by the medical practice management system before a patient visits a medical practice according to the present invention.
Figure 3C:
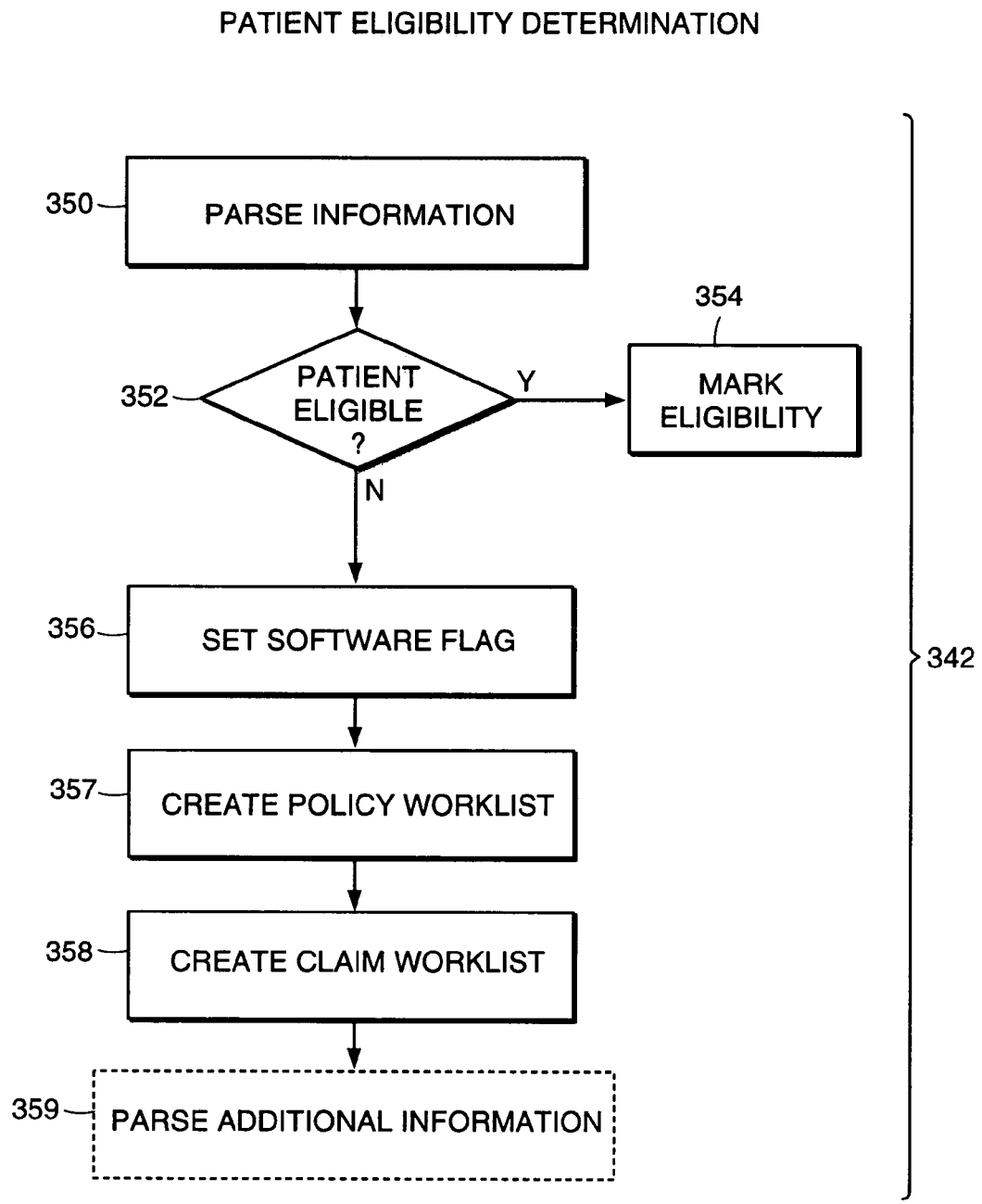
FIG. 3C illustrates an embodiment of the steps performed by the medical practice management system to determine patient eligibility.

Also referring to FIG. 3C, when the ITR module 68 receives the eligibility information from the payor server 18, the workflow processing engine 56 parses the information (step 350) to determine whether or not the patient is eligible (step 352). If the patient is eligible, the workflow processing engine 56 marks the patient's eligibility, such as on the patient registration screen 400 (step 354). Further, if the patient is not eligible, the workflow processing engine 56 sets a particular software flag (e.g., not eligible flag) on the associated insurance policy (step 356). In a further embodiment, the workflow processing engine 56 searches the insurance plans to create a policy worklist for the medical provider (step 357). Moreover, the workflow processing engine 56 copies all of the claims associated with that patient to create a claim worklist (step 358). This worklist has to be cleared before the workflow processing engine 56 can use the ITR module 68 to transmit the claim to the payor server 18. Moreover, the workflow processing engine 56 may additionally parse additional information out of the eligibility information, such as the copayment amount (step 359). Although described above as the workflow processing engine 56 performing these tasks, any of the other components of the medical practice management server 14 (e.g., rules engine 60) can alternatively or collaboratively perform these tasks.

Referring again to FIG. 3B, in yet another embodiment, the workflow processing engine 56 stores insurance information for each established patient in the insurance information database 96 and updates the insurance information database 96 regularly at predetermined intervals. The workflow processing engine 56 can search the insurance information database 96 to verify the insurance eligibility of the patient (step 336). The workflow processing engine 56 can then alert the medical care provider about the patient's eligibility (step 340), such as with a message advising the medical care provider to call the insurance company directly to verify that the patient has valid insurance.

In one embodiment, the workflow processing engine 56 also receives referral information associated with the patient (step 344) and subsequently verifies the referral information to ensure that the patient is referred by the medical care provider quoted by the patient (step 336).

Figure 3D:
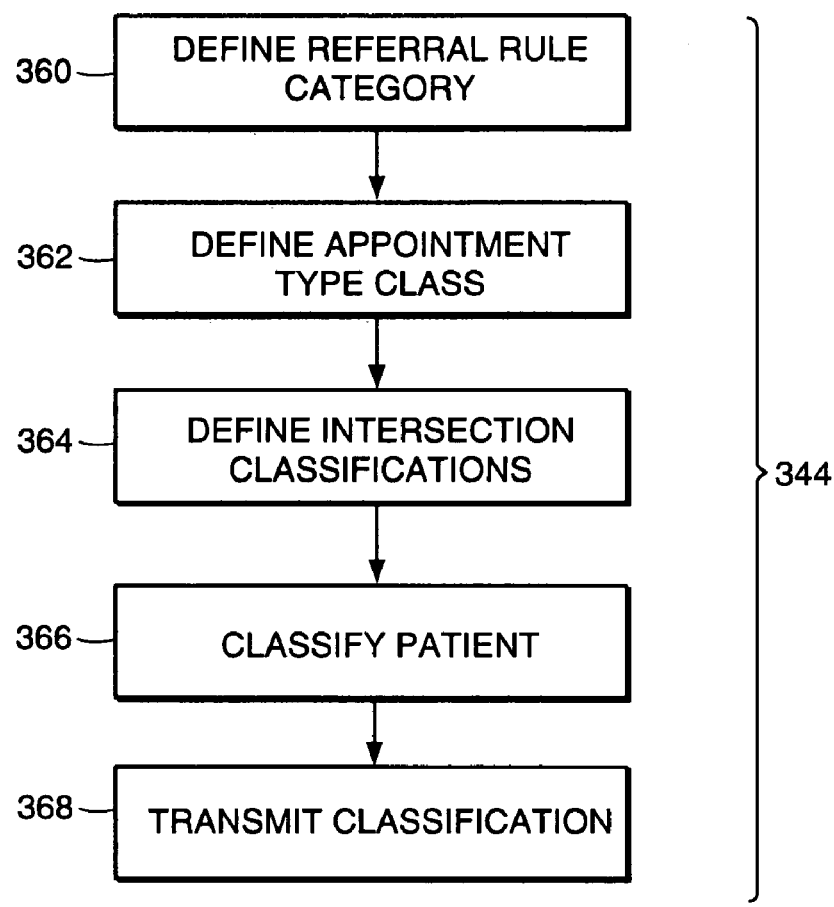
FIG. 3D illustrates an embodiment of the steps performed by the medical practice management system to determine patient referral/prior authorization information.

Also referring to FIG. 3D, to determine whether a patient's particular visit requires a referral, the rules engine 60 defines two constructs: a referral rule category and an appointment type class (step 360 and step 362). The rules engine 60 groups particular payor organizations into referral rule categories. The rules engine 60 also maps particular appointment types within medical practices onto an appointment type class. The workflow processing engine 56 then defines the intersection of a given referral rule category and a particular appointment type (step 364) to either require a referral/preauthorization, not require a referral/preauthorization, or maybe require a referral/preauthorization. The workflow processing engine 56 then classifies a patient into one of these intersection classifications (step 366) and transmits the referral classification (e.g., referral not required) to the medical practice client 10 (step 368). If a referral/preauthorization is required but does not exist, the workflow processing engine 56 does not submit the claim and waits for further updates/edits (i.e., sets the claim status to HOLD, as described further below). Thus, the result of the referral/preauthorization classification, like all other information/results, can be used various and numerous times throughout one or more workflows without limit to the invention.

In further embodiments, the ITR module 68 automatically initiates a referral inquiry with the payor server 18 if the workflow processing engine 56 determines that the patient requires a referral/preauthorization.

The medical care provider then schedules an appointment with the patient. As shown in FIG. 3B, the workflow processing engine 56 receives the proposed schedule appointment (step 346) and simultaneously verifies that the proposed schedule date is appropriate (step 336). For instance, if the medical care provider incorrectly enters that the scheduled date is in the year 2000 instead of the year 2001, the workflow processing engine 56 catches the typographical error and alerts the medical care provider about the error (step 340). In additional embodiments, the workflow processing engine 56 confirms the appointment (step 348) by displaying a confirmation screen on the medical practice client 10.

Figure 3E:
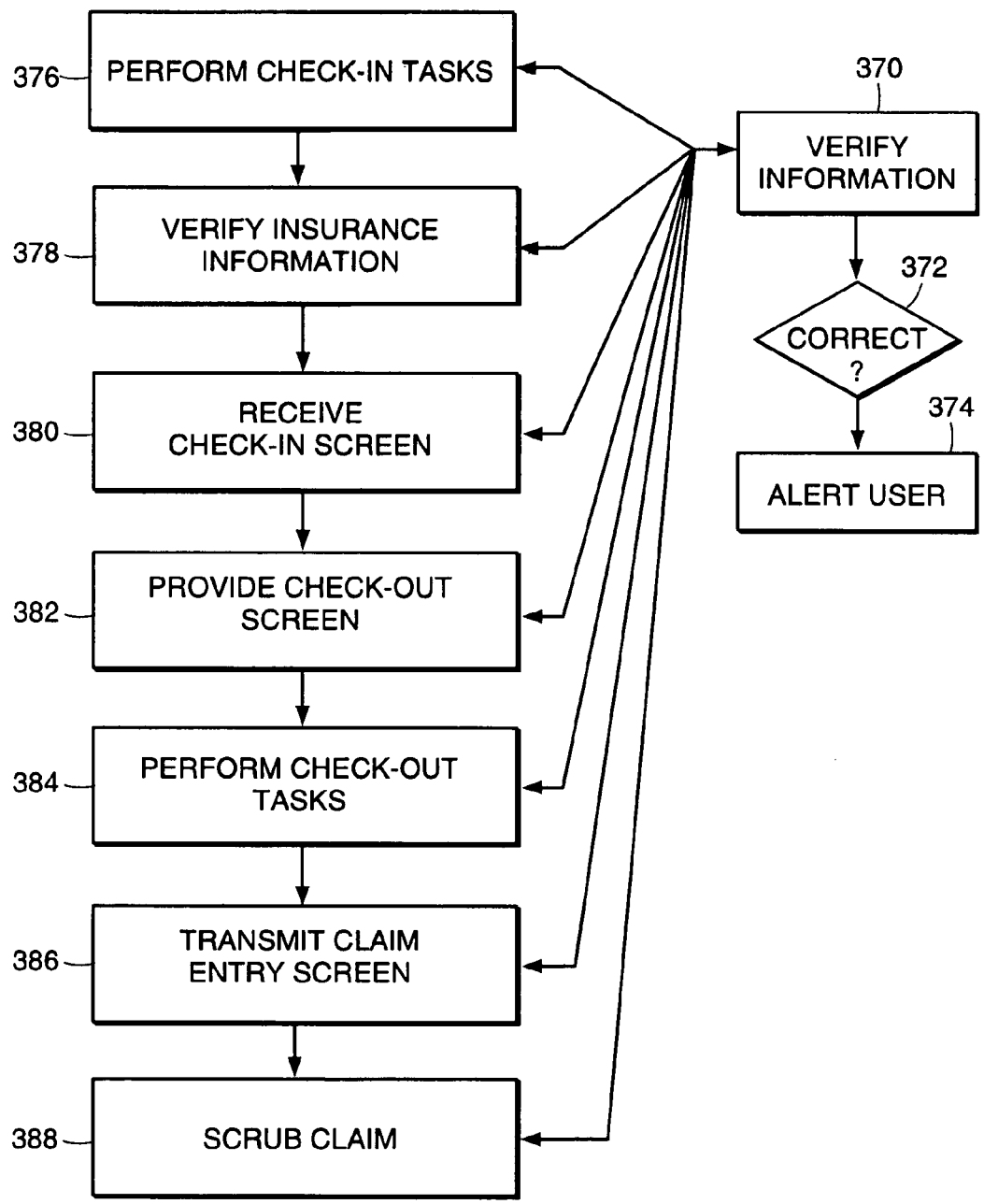
FIG. 3E illustrates an embodiment of a patient workflow diagram performed by the medical practice management system while a patient visits a medical practice according to the present invention.

Subsequently, the patient visits the medical practice. Referring to FIG. 3E, the medical practice client 10 and the workflow processing engine 56 perform their respective tasks associated with patient check-in (step 376). In one embodiment, the medical care provider transmits a request for a check-in screen to the medical practice management server 14, such as by clicking on the name of the patient on the medical practice user interface 36. The workflow processing engine 56 transmits a check-in screen to the medical practice client 10 for input by the medical care provider. An exemplary check-in screen 500 is illustrated in FIG. 5 and is described in more detail below.

The medical care provider enters patient information into the check-in screen. The workflow processing engine 56 verifies all information entered into the check-in screen (step 370) without intervention from the medical provider. This verification can occur in real-time, i.e., while the medical care provider enters the information into the check-in screen, or after the medical care provider completes the patient check-in screen and submits it to the medical practice management server 14 (as described below). Further, in one embodiment, the server 14 (i.e., the workflow processing engine 56) does not accept a check-in screen until all of the required patient information for that patient is complete.

In one embodiment, the patient check-in screen enables the medical care provider to edit (e.g., update) the insurance information received during the tasks performed before the patient's visit. Upon an edit, the workflow processing engine 56 verifies the insurance information (step 378) to determine if any inaccuracies exist and can alert the medical care provider (step 374) upon a finding of an error.

The medical care provider then collects the copayment from the patient for the visit to the medical practice and enters the amount of the copayment into the check-in screen. In one embodiment, the medical care provider then submits the check-in screen to the medical practice management server 14. The workflow processing engine 56 receives the check-in screen (step 380) and, in one embodiment, verifies all of the information entered into the patient check-in screen (step 370).

Figure 6:
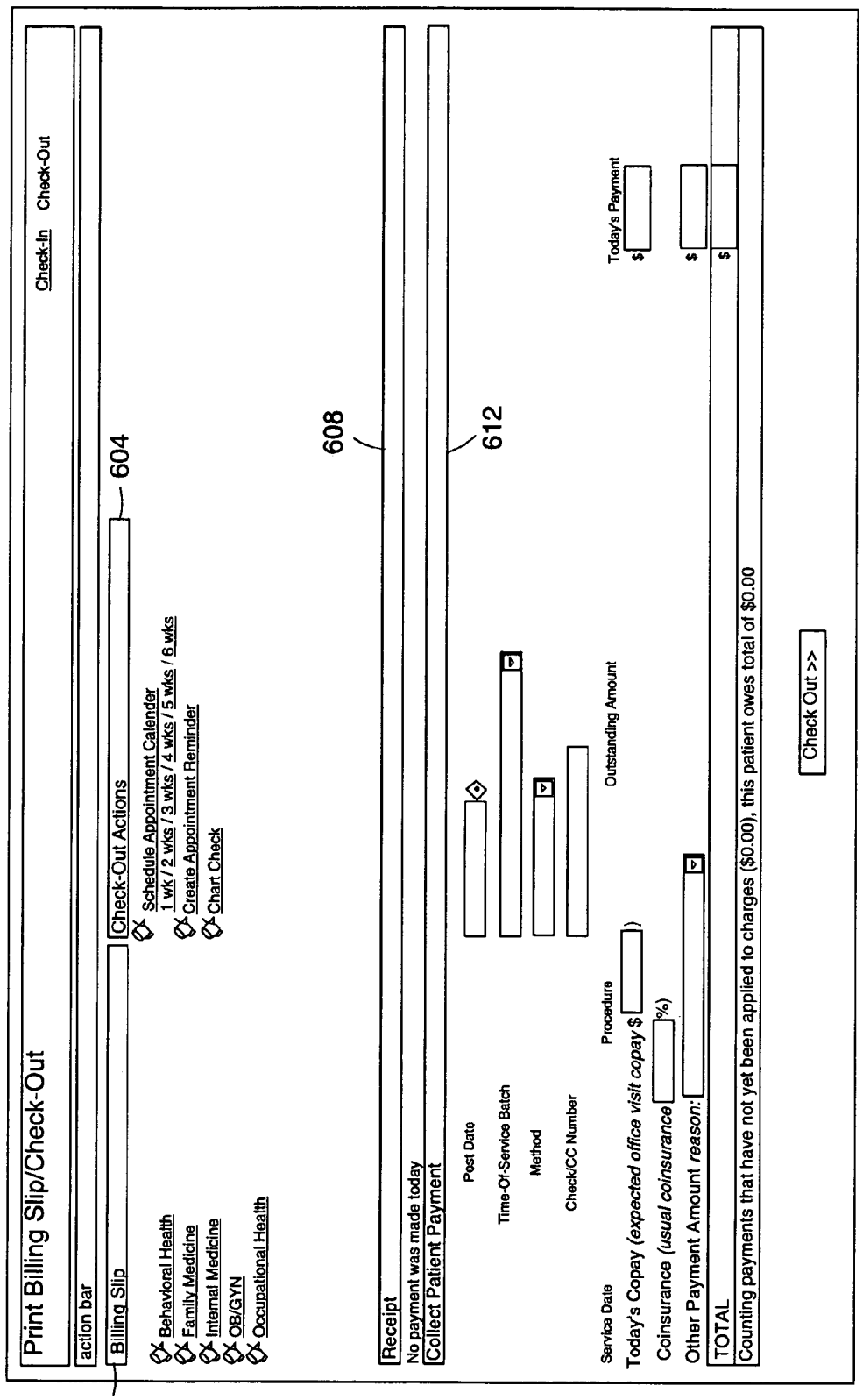
FIG. 6 illustrates an exemplary embodiment of a patient check-out screen according to the present invention.

The workflow processing engine 56 then transmits a check-out screen to the medical practice client 10 (step 382). An exemplary check-out screen 600 is illustrated in FIG. 6 and is described in more detail below. In one embodiment, the medical care provider then provides a billing slip to the patient for the services incurred.

Once the patient is prepared to leave the medical practice, the medical care provider and the workflow processing engine 56 perform check-out tasks (step 384). For instance, these check-out tasks include, without limitation, rescheduling an appointment, creating an appointment reminder, and creating a chart check. A chart check is a systematic way to keep track of patients needing follow up. At each of these tasks, the workflow processing engine 56 automatically verifies that the information is correctly entered (step 370) and alerts the medical practice client 10 if there is some sort of error (step 374). After the check-out task are complete, the medical care provider submits the check-out screen to the medical practice management server 14.

Figure 7A:
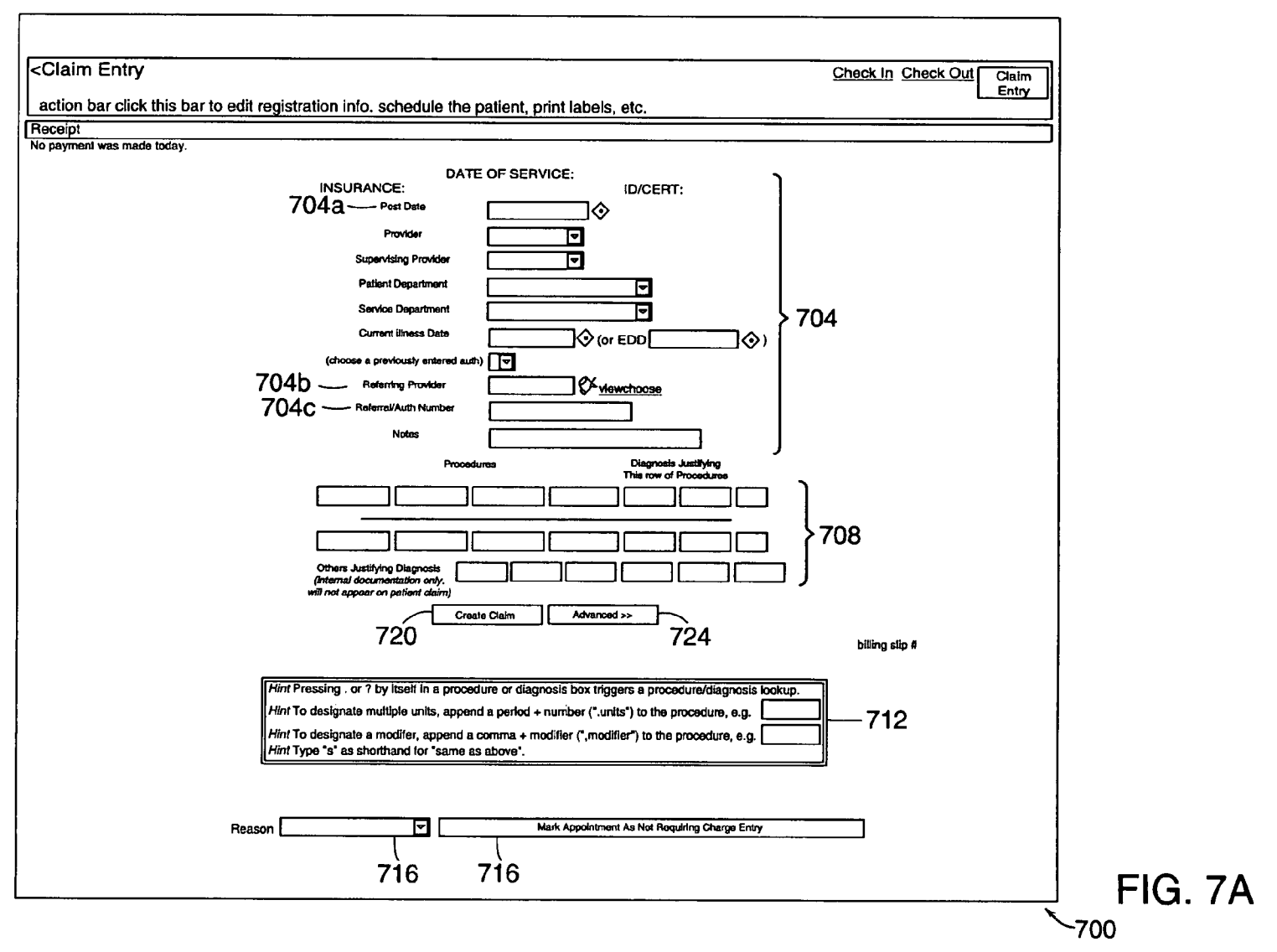

The workflow processing engine 56 then transmits a claim entry screen to the medical practice client 10 (step 386) after receiving the check-out screen. An exemplary claim entry screen 700, or claim entry form, is illustrated in FIG. 7A. Alternatively, the workflow processing engine 56 transmits an advanced claim entry form to provide additional features, such as the advanced claim entry form 732 shown in FIG. 7B. The medical care provider uses the claim entry screen to complete a patient charge entry for the particular patient who had just checked out of the medical practice.

Figure 3F:
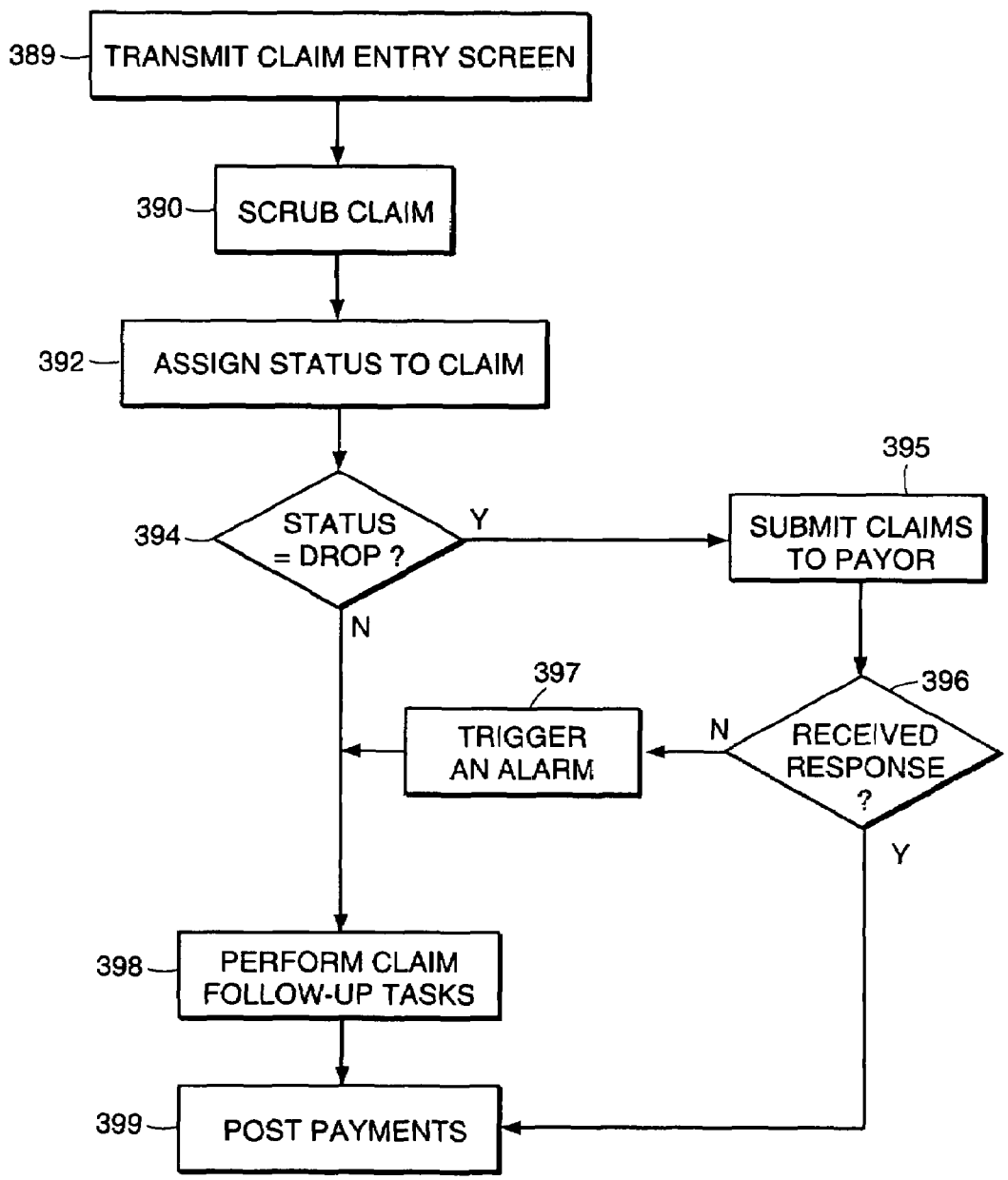
FIG. 3F illustrates an embodiment of a billing workflow diagram performed by the medical practice management system according to the present invention.

The creation of a claim links the tasks performed in FIG. 3E by the medical practice management server 14 during the patient's visit with the tasks performed in FIG. 3F by the server 14 during the billing process. In one embodiment, the start of the creation of a claim occurs following check-out of the patient and continues into the billing workflow of the medical practice management system 5. Also referring to FIG. 3F, when the medical care provider completes the claim entry form, the medical care provider submits the claim entry form to the server 14.

The workflow processing engine 56 transmits the claim entry form (step 389), which ultimately becomes the claim, to the rules engine 60. The rules engine 60 "scrubs" the claim (step 390), or examines the claim for claim errors. Claim errors can include, without limitation, typographical errors, formatting errors (based on a format that each payor defines for their claims), incomplete information, and the like. As described above, the payor server 18 and/or the rule specialists can update the rules database 66 with new or updated rules. Thus, the rules engine 60 can apply different rules to a claim at different times, depending on if the rules database 66 is updated or changed during the life of the claim.

Upon creation of a claim, the workflow processing engine 56 assigns a claim status to the claim (step 392). In one embodiment, the claim status denotes the results of the scrubbing of the claim. The possible claim statuses upon creation of the claim are shown in the table below:

| Claim Status | Description |
|---|---|
| DROP | Identifies claims that are ready to be billed |
| HOLD | Identifies claims that have not passed the scrubbing done by the rules engine due to simple errors |
| MGRHOLD | Identifies claims that have not to passed the scrubbing done by the rules engine due to more detailed claims errors, such as a missing provider number |
| CLOSED | Identifies claims that have a zero balance |

The workflow processing engine 56 then transmits a claim review screen to the medical practice client 10 illustrating the errors in the claim. An exemplary claim review screen 756 is illustrated in FIG. 7C. In one embodiment, these errors must be resolved before the medical practice management server 14 can process the claim. Moreover, in one embodiment the workflow processing engine 56 assigns some sort of HOLD status (e.g., MGRHOLD) to the incorrect claim to denote that the claim cannot currently be transmitted to the payor server 18.

In another embodiment, the medical care provider enters charges for multiple patients that have visited the medical practice within a predetermined amount of time (e.g., on a particular day). This is also referred to as entering a batch submission of patient charges. In one embodiment, this option is available in the advanced claim entry form shown in FIG. 7B.

The workflow processing engine 56 then determines if the claim has its claim status set to DROP (step 394). If so, the workflow processing engine 56 submits the claim to the payor (i.e., payor server 18) using the ITR module 68 (step 396). In one embodiment, the workflow processing engine 56 also communicates with a central billing office (CBO) (not shown). The CBO generates and submits the claims to the payor. The CBO transmits the claim to the payor server 18 over the payor server network 34. In yet another embodiment, if the payor associated with the claim is not accessible via the payor server network 34, the CBO transmits a paper version of the claim to the payor. Once the claim is transmitted to the payor (via the payor server network 34 or on paper), the workflow processing engine 56 changes the status of the claim to BILLED. It should be noted that the workflow processing engine 56 could perform the tasks that the CBO performs.

In further embodiments, the workflow processing engine 56 places an alarm on the claim to enable a high level of control and management of the claims. Typically, a user of a billing system executes a report on the age of the claim and performs work on the claims that are older than a predetermined time. In one embodiment, the medical practice management server 14 includes this functionality. However, the medical practice management server 14 can alternatively use alarms with the claims to control and manage the claims.

The alarm placed on the claim could depend on the particular claim clearinghouse used and/or on the particular payor. Additionally, the workflow processing engine 56 determines in step 396 the time that the claim is submitted to the payor. If the ITR module 68 does not receive a response from the payor server 18 within a predetermined amount of time, the workflow processing engine 56 triggers the alarm. Upon the triggering of the alarm, the workflow processing engine 56 moves the claim into a claim inquiry grouping of claims. The claim inquiry grouping of claims are claims that must be followed up on by, for instance, the CBO or by the workflow processing engine 56. Additionally, the workflow processing engine 56 may also set the claim status to BILLED and may place another alarm on the claim. This alarm is a function of the insurance and a "kickreason". A "kickreason" is a code that the workflow processing engine 56 sets to describe what has to be done to the claim to resolve the claim. In further embodiments, this code is insurance-specific.

The workflow processing engine 56 and/or the ITR module 68 then performs claim follow-up tasks (step 398). In one embodiment, as part of the claims follow-up tasks, the workflow processing engine 56 transmits a claim edit screen to the medical practice client 10 to enable the medical care provider to correct the claims that have errors. An exemplary claim edit screen 768 is illustrated in FIG. 7D and is described in more detail below. In another embodiment, the claim edit screen includes an explanation portion to explain the claim errors to the medical care provider. An exemplary explanation portion 770 of the claim edit screen 768 is illustrated in FIG. 7E. The medical care provider updates the claim based on the errors denoted in the claim review screen 756 and/or the explanation portion 770 of the claim edit screen 768. In one embodiment, the rules engine 60 scrubs the claim again following the editing by the medical care provider and the workflow processing engine 56 assigns a DROP status to the claim if no errors are found.

Additionally, once the medical care provider starts to receive payments for the claims, the medical practice management server 14 applies these payments against the associated charges. More specifically, the workflow processing engine 56 "posts" the payment for the associated claim (step 399). Furthermore, the workflow processing engine 56 can then assign a claim status of CLOSED to the claim associated with the payment that has been posted.

Furthermore, in other embodiments, the medical practice management server 14 can generate, transmit, and display reports to the medical practice client 10 about the medical practice. For instance, the workflow processing engine 56 can provide a report illustrating the medical practice's accounts receivable by date of service. Alternatively, the workflow processing engine 56 can search the patient information database 92 to provide a report of the demographic makeup of the patient population of the medical practice.

Referring to FIG. 4, an exemplary registration screen 400 includes a patient registration information section 404 and a notes section 408. The patient registration information section 404 can include any information required by the medical practice to register the patient. Examples of patient registration information included in section 404 are, without limitation, the patient's name, address, social security number, phone number, employer, and the like. The notes section 408 includes a section for the medical provider (e.g., receptionist) to provide any sort of notes about the patient.

Referring to FIG. 5, a check-in screen 500 includes a view/cancel appointment section 504, an edit appointment information section 508, an insurance section 512, a verify and edit registration information section 516, and a collect patient payment section 520. These sections are for illustrative purposes only and can be altered and/or replaced to provide whatever information is required for checking a patient into the medical practice.

An exemplary check-out screen 600 is illustrated in FIG. 6. In one embodiment, the check-out screen 600 is divided into several sub-sections: the billing slip sub-section 602, the check-out actions 604, the receipt sub-section 608, and the collect patient payment subsection 612. If the medical care provider collects a billing slip from the patient, the medical care provider can select the receipt sub-section 608 and provide a receipt to the patient for the services incurred.

FIG. 7A illustrates an exemplary claim entry screen 700. The claim entry screen 700 includes a patient claim information section 704, a procedure section 708, a hint section 712, and a non-claim resulting button 716. In one embodiment, the patient claim information section 704 includes information such as the claim post date field 704a, a referring provider name field 704b, and a referral number field 704c. The procedure section 708 typically includes a location in which the medical provider can enter in a procedure number denoting the medical procedure performed on the patient during the patient visit. The medical provider can use the non-claim resulting button 716 to denote the appointment as not requiring the creation of a claim.

In further embodiments and as shown, the workflow processing engine 56 includes a create claim button 720 and an advanced claim button 724 in the claim entry screen 700. The medical provider hits the create claim button 720 after the claim entry form 700 is completely filled out. If a field of a section 704, 708, 712, 716 is empty and the medical provider hits the create claim button 720, the workflow processing engine 56 can denote that the claim is not complete to the medical provider. In another embodiment, the workflow processing engine 56 looks up patient information from the patient information database 92 and completes as many of the fields in the claim entry form 700 as possible.

Figure 7B:
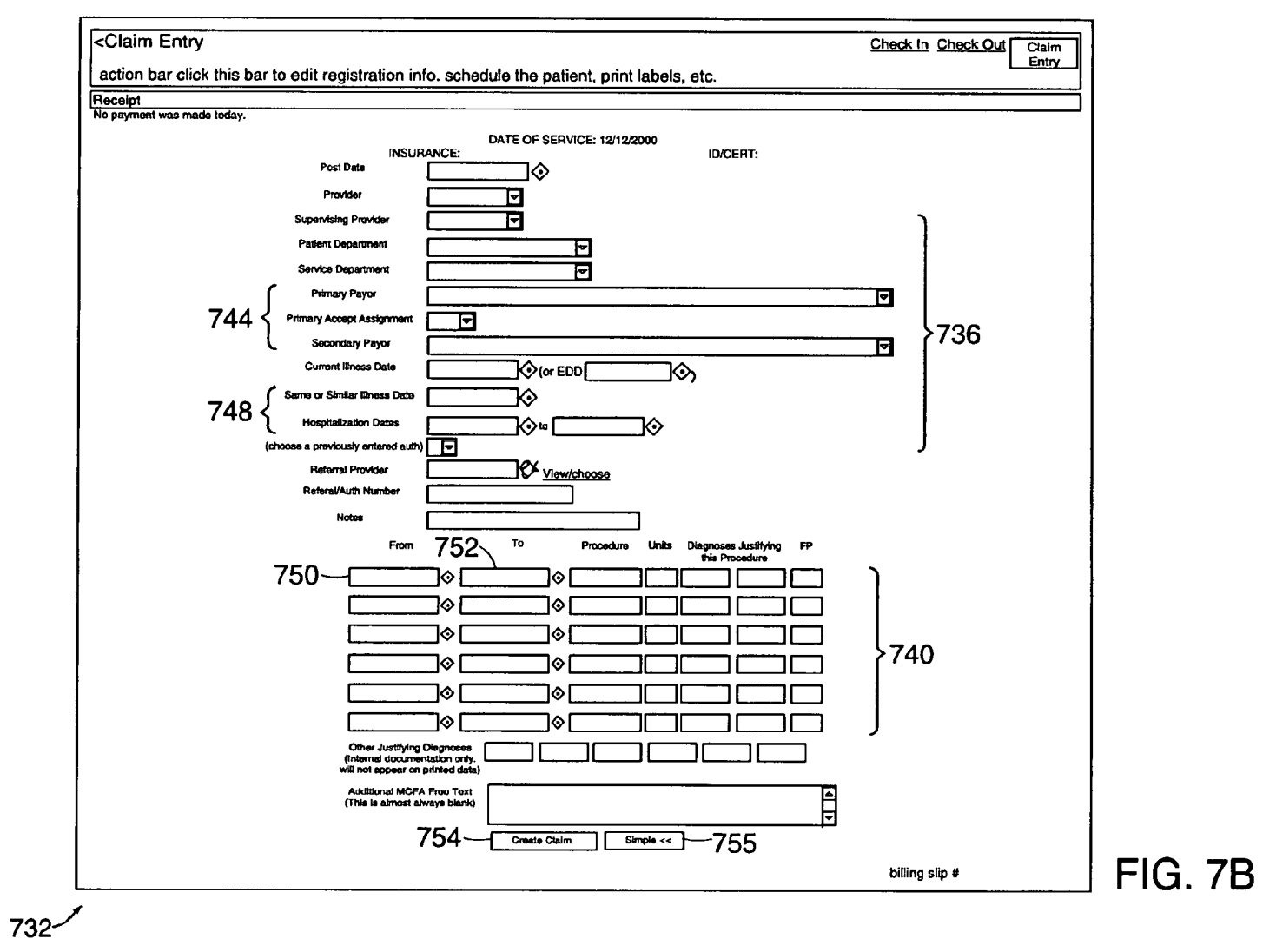
Figure 7C:
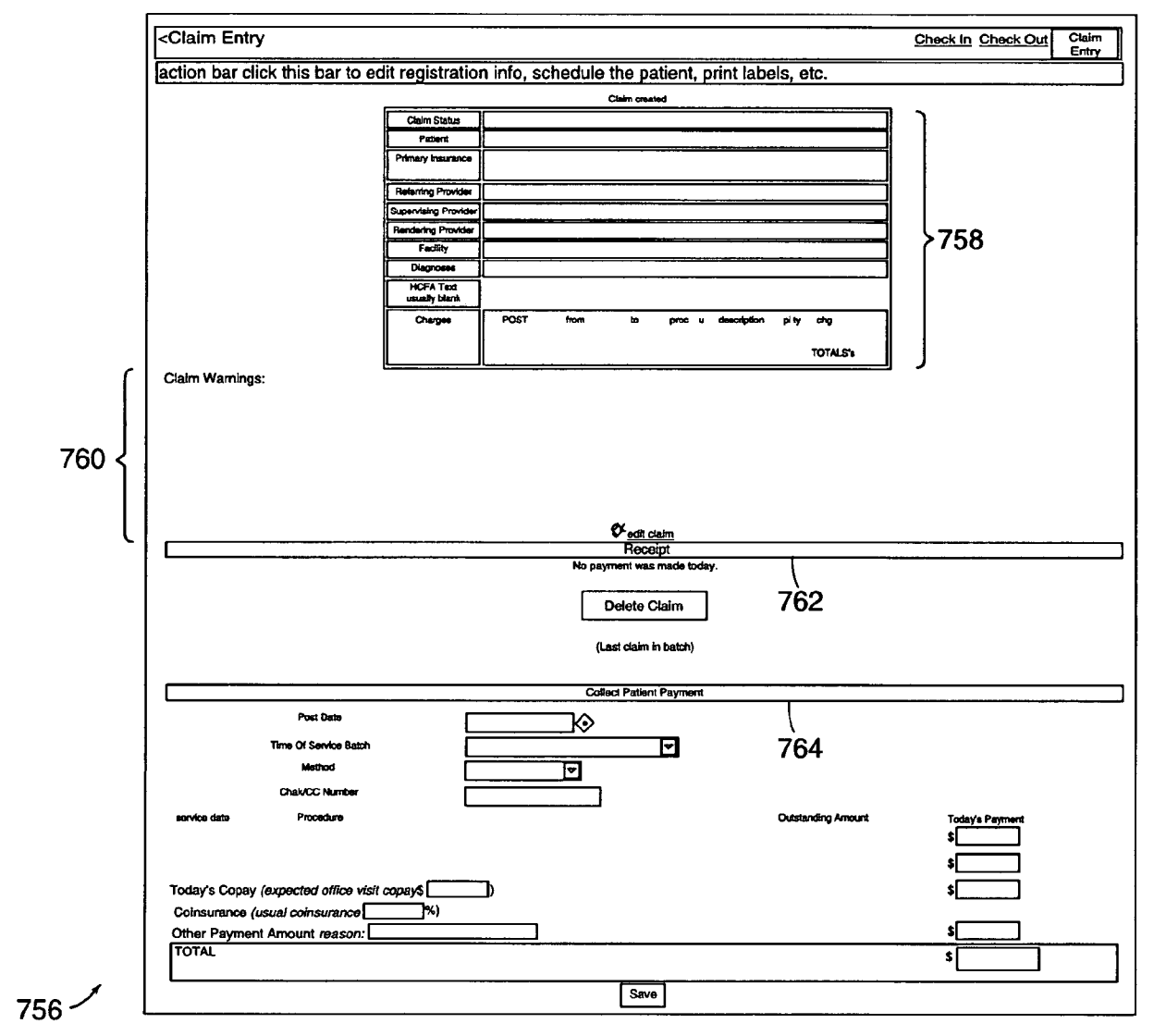
Figure 7D:
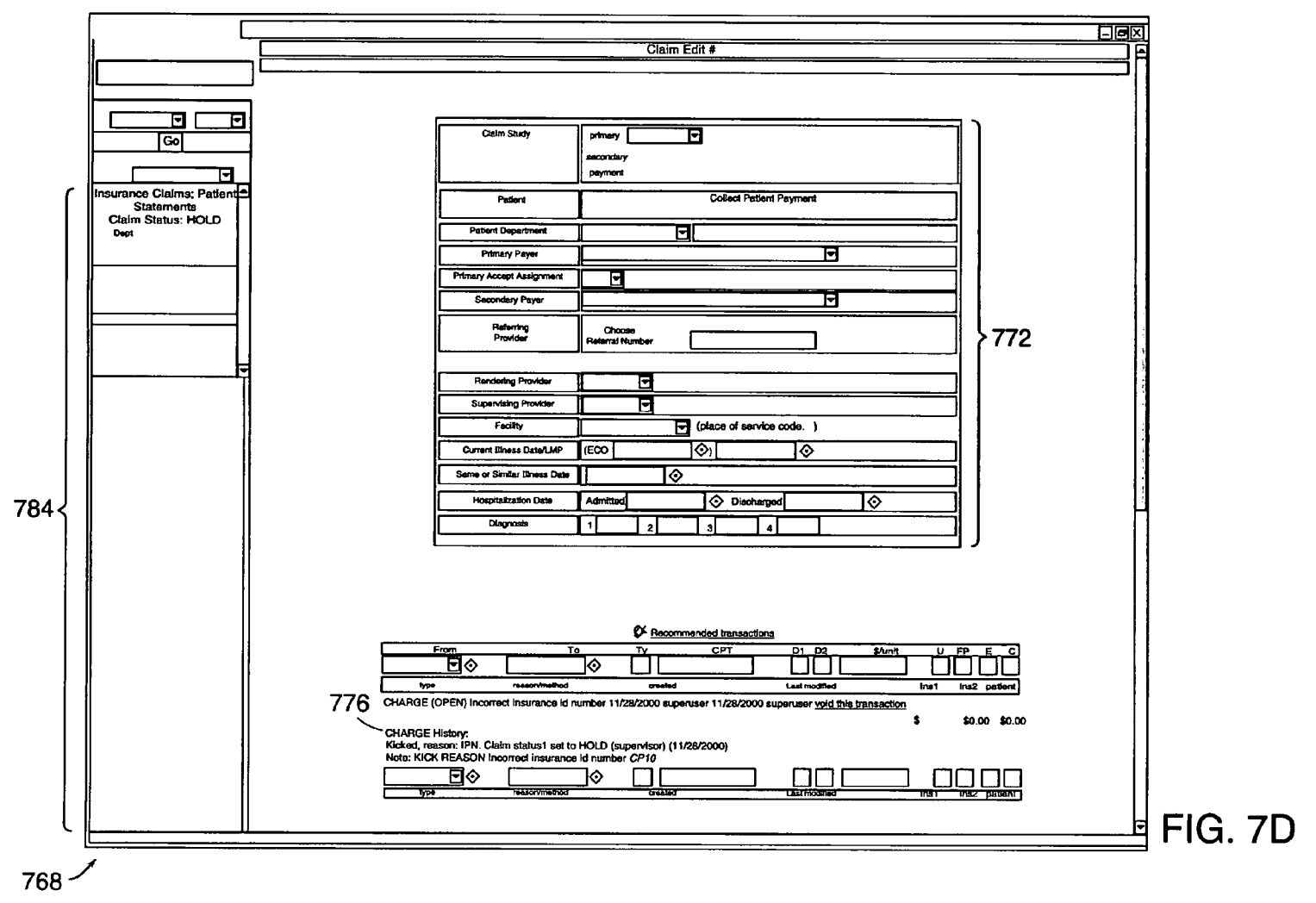
Figure 7E:
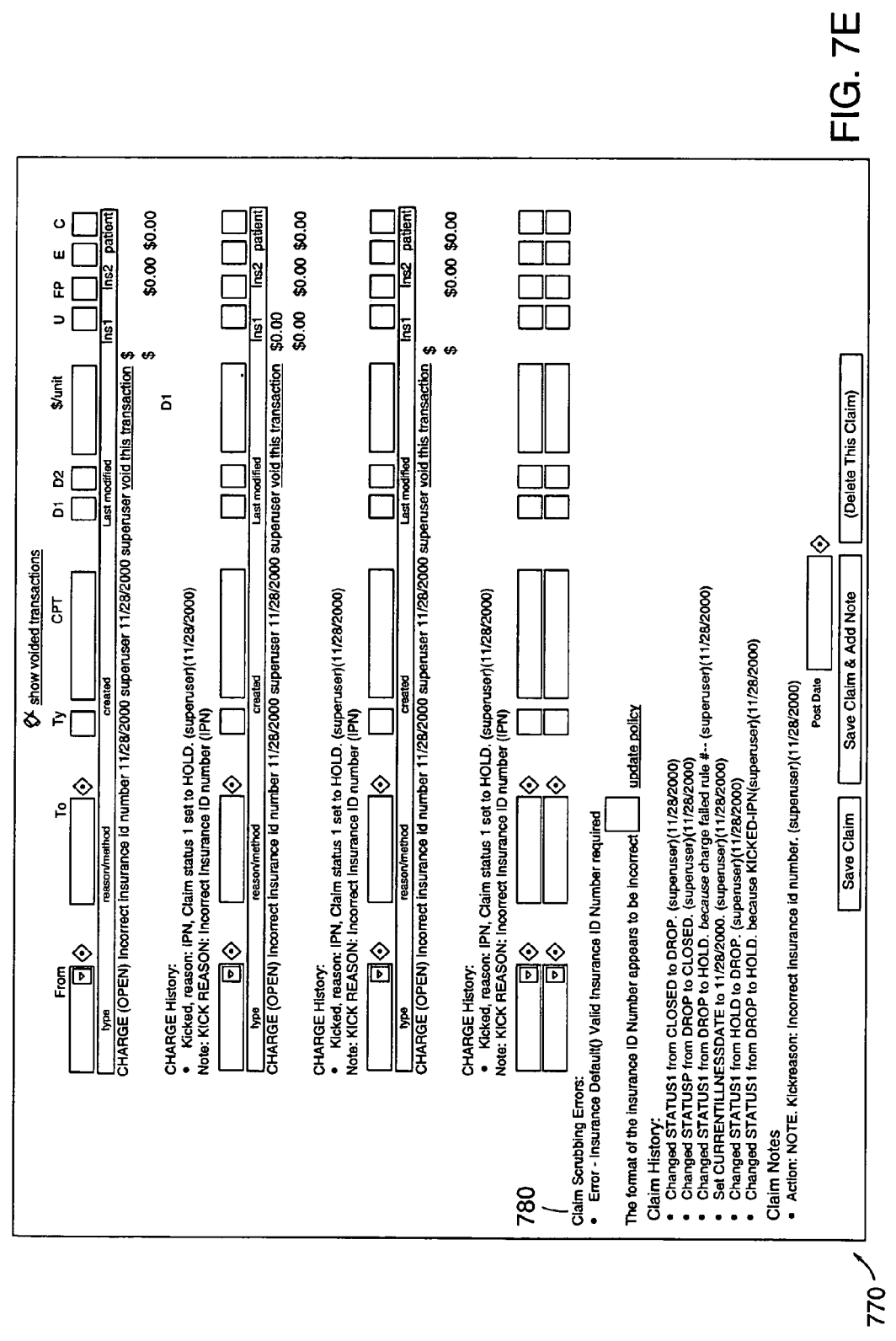

In one embodiment, referring to FIG. 7B, if the medical provider hits the advanced claim button 724, the workflow processing engine 56 provides an advanced claim screen 732 to the medical practice client 10. The advanced claim screen 732 includes an advanced patient claim information section 736 and an advanced procedure section 740. The advanced patient claim information section 736 can include, for instance, a payor section 744 and an illness section 748. Moreover, the advanced procedure section 740 can include a range 750, 752 of dates in which a procedure was performed. It should be noted that any modifications to the advanced claim entry form 732 (e.g., additional information) can be included in the advanced claim entry screen 732. The advanced claim entry form 732 can also include a create claim button 754, as described above, and a simple claim button 755 to retrieve the claim entry screen 700 shown in FIG. 7A.

FIG. 7C illustrates a claim review screen 756 having a created claim summary section 758, a claim warnings section 760, a receipt section 762, and a payment section 764. The workflow processing engine 56 denotes warnings associated with the claim in the claim warnings section 760. Claim warnings could include messages such as "The supervising provider has no id number entered for the given insurance" or "The second procedure is a component of the first procedure. These codes may not be billed together." The receipt section 762 illustrates receipts that the workflow processing engine 56 can provide to the medical practice client 10. The payment section 764 includes information about payments received by the medical practice management server 14.

Referring to FIG. 7D and 7E, a claim edit screen 768 and a claim error explanation portion 770 of the claim edit screen 768 is shown. Alternatively, the claim edit screen 768 and the claim error explanation portion 770 are joined into one screen. The claim edit screen 768 and the claim error explanation portion 770 include a claim edit section 772, a charge history section 776, and a claim scrubbing error section 780 to enable efficient edits of the claims. A summary 784 of the charge history section 776 can also be included in the claim edit screen 768.

Figure 8A:
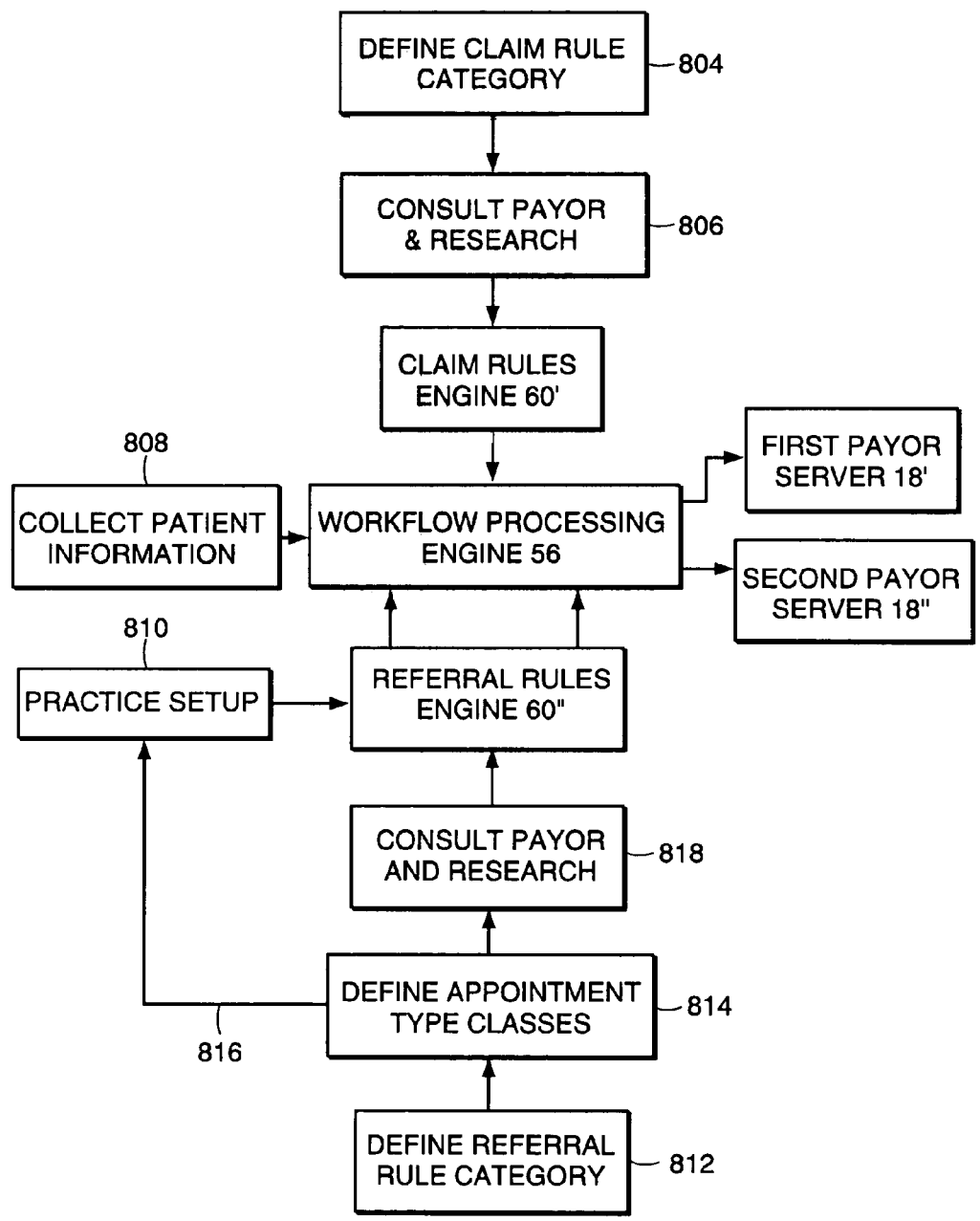
FIG. 8A illustrates an exemplary embodiment of the communications performed by several of the components of the medical practice management system according to the present invention.

An exemplary embodiment of the communications performed by several of the components of the medical practice management system 5 is illustrated in FIG. 8A. A rules specialist, as described above, defines a claim rule category to classify particular rules into a particular group for application with particular claims (step 804). The rules specialist then consults with (e.g., converses with) the payors (e.g., the payor servers 18) to obtain information related to the payor organization (step 806). In one embodiment, the consultation is human communication. In another embodiment, the consultation is communication between the payor server 18 and the medical practice management server 14. Further, the rules specialist could also perform research on the payor organization to further fine-tune information associated with the payor organization, such as the claim rule category (step 806). This rules specialist then inputs this information into the rules engine 60.

In one embodiment, the rules engine 60 is further divided into categorized rules engines, such as a claim rules engine 60' and a referral rules engine 60". In one embodiment, the rule specialist inputs the claim rule information into the claim rules engine 60' for future application with a claim (e.g., produced by the workflow processing engine 56).

Besides receiving information from the claim rules engine 60' (e.g., upon application of claim rules), the workflow processing engine 56 also receives and transmits information from/to various other sources. For instance, the workflow processing engine 56 collects the patient information from the medical practice client 10 (step 808). Another step implemented by the workflow processing engine 56 is the collection of practice setup information (step 810). In one embodiment, the workflow processing engine 56 receives practice setup information from practice setup specialists. Examples of practice setup information include, without limitation, payor organization locations, departments located within payor organizations, payor identification information, and the like. In a further embodiment, the medical practice client 10 provides the practice setup information to the workflow processing engine 56. The workflow processing engine 56 also communicates with one or more payor servers 18, such as a first payor server 18' and a second payor server 18".

A rules specialist also defines a referral rule category and appointment type classes (steps 812 and 814). In one embodiment, the practice setup specialist (or medical practice client 10) retrieves the appointment type classes for use with the practice setup, as shown with arrow 816. The rules specialist can also consult with (e.g., converse with) and do research on the payor organizations to obtain information related to the payor organization (step 818). The rules specialist then transmits this information into a referral rules engine 60", another categorized rules engine within the rules engine 60 that handles referral rules. When applicable, the referral rules engine 60" applies these referral rules to information associated with the practice setup (step 810) and transmits the result(s) to the workflow processing engine 56.

The communications between the workflow processing engine 56 and the other components of the medical practice management system 5 (e.g., the claim rules engine 60', the referral rules engine 60", the payor servers 18', 18", and the medical practice client 10) can occur before, during, after, and between one or more tasks performed by the workflow processing engine 56. One or more of the communications can occur simultaneously with any of the other communications.

Figure 8B:
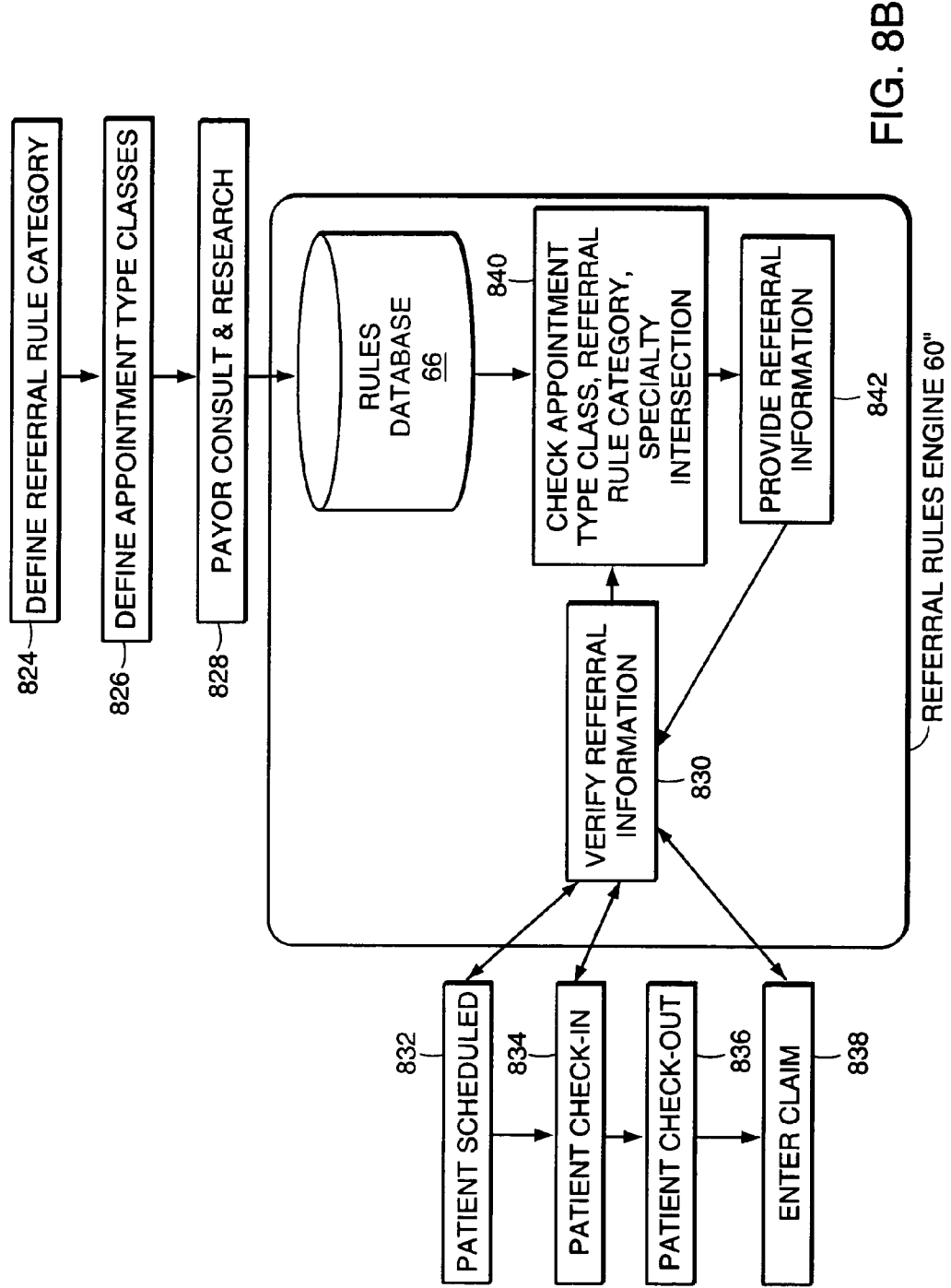
FIG. 8B illustrates an exemplary embodiment of the tasks performed by the workflow processing engine and a referral rules engine according to the present invention.

An embodiment of the tasks performed by the workflow processing engine 56 and the referral rules engine 60" is illustrated in FIG. 8B. The rules specialist defines the referral rule category (step 824) and/or the appointment type classes (step 826) and stores the information in the rules database 66 (of the referral rules engine 60"). Additionally, the workflow processing engine 56 and/or the rules specialist can consult with the payor organization to obtain information related to the payor (step 828). Although shown as a linear workflow diagram, the above mentioned steps can be performed linearly or in parallel to one or more of the other steps.

The workflow processing engine 56 may perform one or more tasks in which the referral rules engine 60" verifies the referral information (step 830). An embodiment of the tasks performed during a rules referral include the workflow processing engine 56 scheduling a patient (step 832), checking a patient into the medical practice 10 (step 834), checking a patient out of the medical practice client 10 (step 836), and entering (step 838) a claim for the patient.

During the verification of the referral information, the referral rules engine 60" checks one or more of the appointment type class, referral rule category, and specialty intersection (step 840). Once the referral rules engine 60" checks these items, the referral rules engine 60" provides referral information to the workflow processing engine 56 (step 842).

Figure 8C:
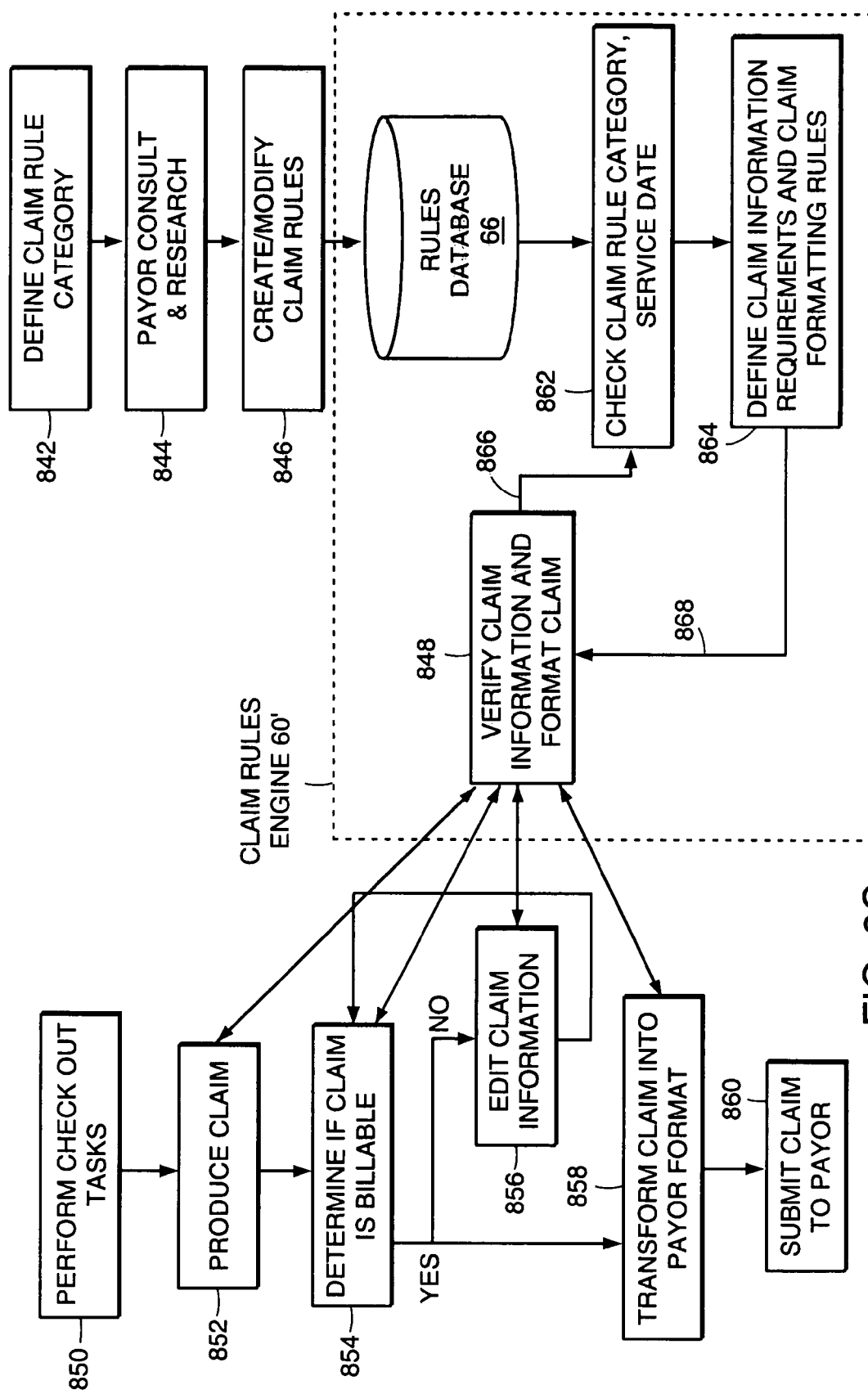
FIG. 8C illustrates an exemplary embodiment of the tasks performed by a claim rules engine 60 and the workflow processing engine according to the present invention.

An embodiment of the tasks performed by the claim rules engine 60' and the workflow processing engine 56 is shown in FIG. 8C. As described above, a rules specialist defines the claim rule category (step 842), consults with and/or does research on the payor (step 844), and creates/modifies the claim rules (step 846). The specialist stores this information into the claim rules engine 60'.

The claims rules engine 60' verifies the claim information and/or formats the claim (step 848) throughout numerous steps performed by the workflow processing engine 56. For instance, following the performance of the check-out tasks (step 850), the workflow processing engine 56 uses the information from the medical practice client 10 (and/or the payor information from the payor server 18) to produce the claim (step 852). The workflow processing engine 56 then determines if the claim is billable (step 854) based on the verification process performed by the claim rules engine 60' in step 848. If not, the workflow processing engine 56 may edit the claim information based on information received from the claim rules engine 60' (e.g., if the claim rules engine 60' provides the workflow processing engine 56 with information relating to edits to be performed to make the claim billable) (step 856).

If the claim is billable, the workflow processing engine 56 transforms the claim into a format acceptable to the payor organization (i.e., the payor server 18) (step 858). As illustrated, the claim rules engine 60' performs the verification and formatting task (step 848) throughout many of the tasks performed by the workflow processing engine 56. Moreover, information transmitted to the workflow processing engine 56 from the verification/formatting task (step 848) of the claim rules engine 60' can be used during any one of the tasks performed by the workflow processing engine 56. The workflow processing engine 56 then submits the claim to the payor after formatting the claim to the payor's specifications (step 860).

During the verification and formatting process performed by the claim rules engine 60', the claim rules engine 60' checks the claim rule category and the service date of the claim (step 862) and uses this information to define claim information requirements and claim formatting rules (step 864). The claims rules engine 60' verifies the claim information and formats the claim(s) (step 848) to facilitate acceptance by the provider. As shown by arrow 866, in one embodiment the claim rules engine 60' checks the claim rule category and service date (step 862) in conjunction with (e.g., before, during, after) the verification process of the claim information and/or during the formatting of the claim (step 848). Additionally, the defining of the claim information requirements and claim formatting rules are used to verify and/or format the claim information, as illustrated with arrow 868.

Figure 8D:
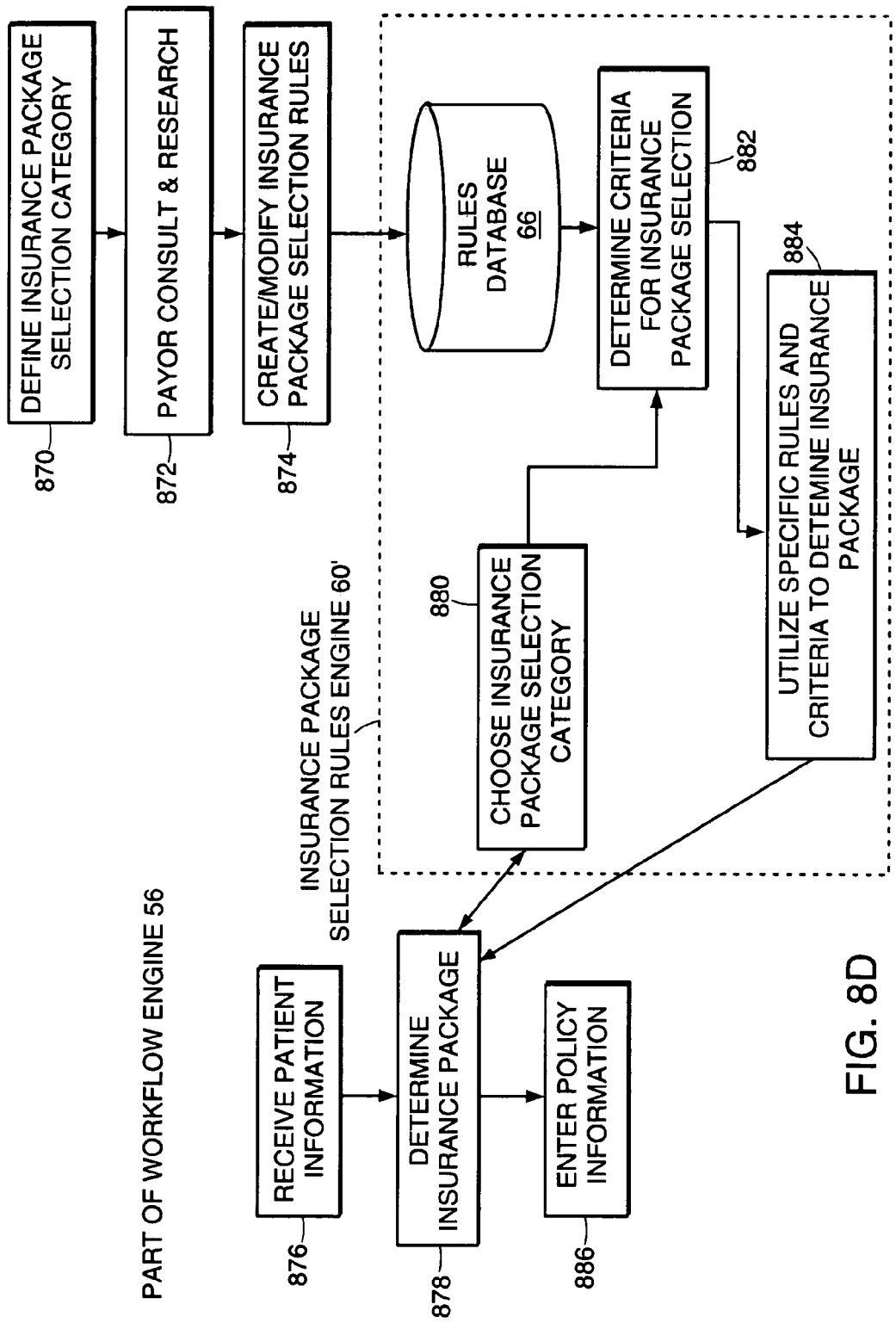
FIG. 8D illustrates an exemplary embodiment of the tasks performed by an insurance package selection rules engine and the workflow processing engine according to the present invention.

In yet another embodiment and referring to FIG. 8D, the rules engine 60 further includes an insurance package selection rules engine 60'''. In one embodiment, an insurance specialist, similar to a rules specialist, enters the insurance information into the insurance package selection rules engine 60'''. In another embodiment, rather than having different specialists (e.g., rules specialist, insurance specialist) to enter the different types of information (e.g., claim rules, insurance rules) into the rules engine 60, one specialist could enter all of the information into the rules engine 60.

In one embodiment, the insurance specialist defines the insurance package selection category and may perform payor consultation and research to determine information about the payor (steps 870 and 872). The insurance specialist then creates/modifies the insurance package selection rules based on this definition and payor consultation (step 874) and transmits the information into the insurance package selection rules engine 6''' (i.e., the rules database 66).

The workflow processing engine 56 receives the patient information from the medical practice client 10 (step 876) and determines which insurance package to use (step 878). This determination involves the insurance package selection rules engine 60''' choosing an insurance package selection category (step 880). The choosing of the insurance package selection category further involves determining criteria for the insurance package selection (step 882), which can be based on the information stored in the rules database 66 (by the insurance specialist). Further, the insurance package selection rules engine 60''' utilizes the specific rules and criteria to determine the insurance package (step 884) for the particular patient. The workflow processing engine 56 uses this information in step 878 and subsequently enters the policy information for the particular patient into a claim (step 886).

Figure 8E:
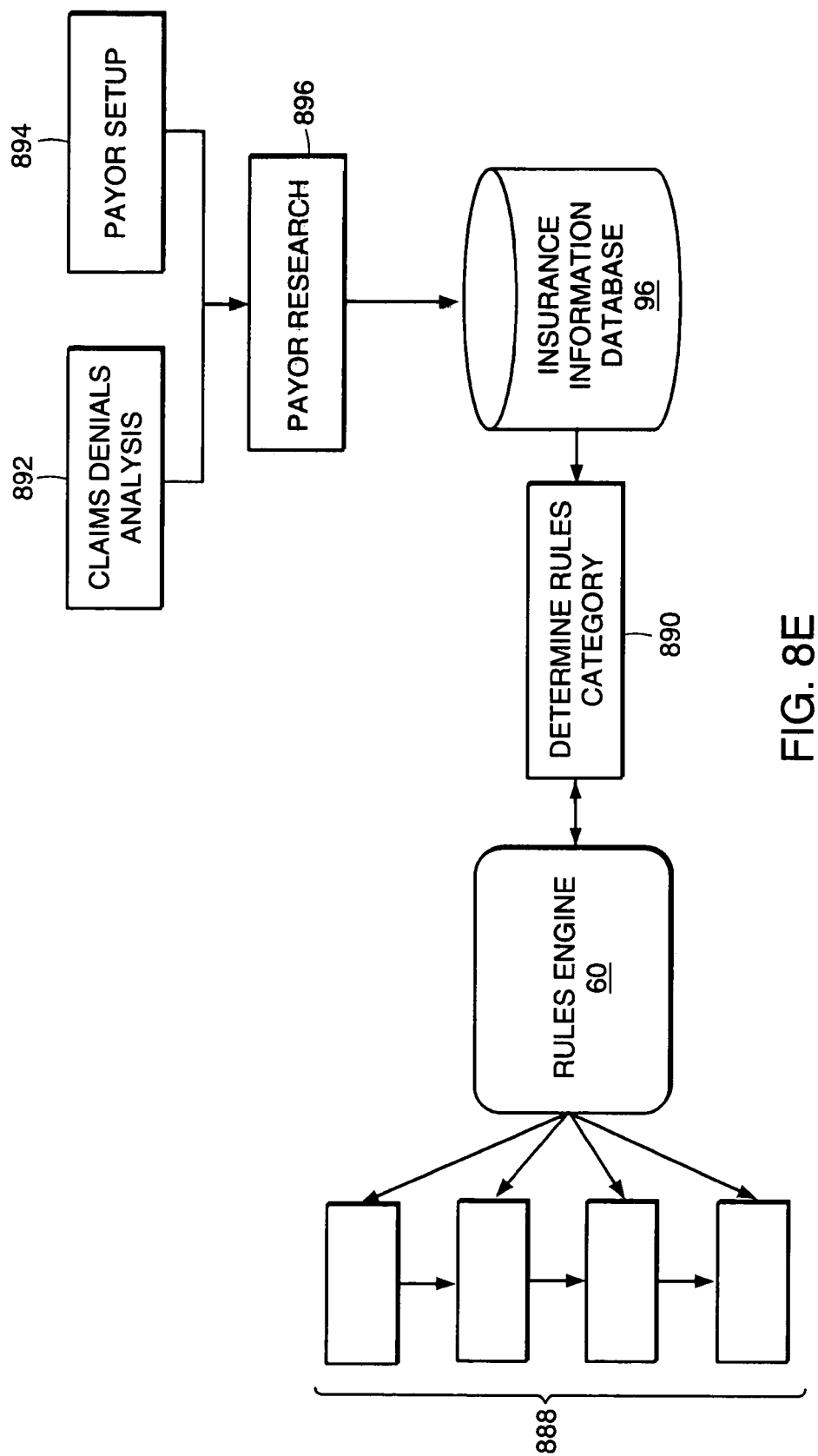
FIG. 8E illustrates an exemplary embodiment of the flow of information into and from the insurance information database according to the present invention.

FIG. 8E illustrates the impact of the insurance information database 96 (as shown in FIG. 2A) on the rules engine 60 and the tasks performed by the workflow processing engine 56. A workflow 888 performed by the workflow processing engine 56 communicates with the rules engine 56 (e.g., the claim rules engine 60', the referral rules engine 60'', the insurance package selection rules engine 60''') at one or more times during one or more of the tasks in the workflow 888. The rules engine 60 applies one or more rules to the information used during the workflow 888. These rules originate from rule categories that, in one embodiment, are defined by specialists (step 890). In another embodiment, the rules engine 60 determines the rules categories. The rules categories are determined from information stored in the insurance information database 96.

In one embodiment, a specialist performs claims denial analysis (step 892) and/or payor setup (step 894) to produce the information for the insurance information database 96. Moreover, a specialist may also perform payor research to obtain more information on the payor organization to aid in attaining accurate rule categories (step 896).

In one embodiment, the insurance information database 96 stores all of the information associated with various payor organizations. Moreover, the information stored in the insurance information database 96 can be used for many functions of the medical practice management system 5. For example, in another embodiment the workflow processing engine 56 uses the information stored in the insurance information database 96 during claim submission.

Further, although some steps illustrated in FIGS. 8A-8E are described as a linear flow of operations, the steps can be performed at various times before, during, or after the performed tasks. The steps illustrated can also be performed simultaneously. Moreover, the information received in one particular step can be used in other steps in the same workflow or other steps in other workflows. Consequently, FIGS. 8A-8E are intended only to illustrate, and not limit, the invention.

The medical practice management system 5 thus increases the efficiency of a medical practice by automatically interacting with information associated with a patient using rules, databases, and/or communication links with payors during the workflow of the medical practice.

While the invention has been particularly shown and described with reference to specific preferred embodiments, it should be understood by those skilled in the art that various changes in form and detail can be made therein without departing from the spirit and scope of the invention as defined by the appended claims.

What is claimed is:

1. A computerized method for managing a medical practice comprising:
   storing by a medical practice management server in a rules database a plurality of insurance rules comprising one or more classes of rules, each class of rules being associated with one of a plurality of payor servers;
   receiving by the medical practice management server data indicative of a completed claim submission for a claim from a medical practice client, the claim being associated with a payor server; and
   automatically interacting with the completed claim submission by the medical practice management server to correct an error in the completed claim submission, wherein the error is resolved by the medical practice client before processing the completed claim submission, by applying one or more rules from a class of rules associated with the payor server, wherein the one or more rules comprises a new rule, an updated rule, or both received from the payor server, the interacting step comprising:
      the medical practice management server automatically associating a first claim status with the completed claim submission indicative of the claim not satisfying one of the one or more rules;
      the medical practice management server transmitting data indicative of a claim edit screen to the medical practice client, the claim edit screen comprising a claim edit section for editing the completed claim submission and a claim error explanation portion to explain one or more errors in the completed claim submission to a medical care provider;
      the medical practice management server receiving data indicative of an updated completed claim submission from the medical practice client;
      the medical practice management server correcting the completed claim submission based on the updated completed claim submission; and
      the medical practice management server automatically associating a second claim status with the completed claim submission indicative of the completed claim submission satisfying all of the one or more rules.

2. The method of claim 1, wherein the error comprises a formatting error of the completed claim submission based on a format defined by the payor server.

3. The method of claim 1, wherein the error comprises a typographical error or incomplete information of the completed claim submission.

4. The method of claim 1, wherein each class of rules of the plurality of insurance rules comprises a rule that has universal applicability to all claims for a payor server associated with the class of rules; a rule that applies to one or more specific insurance packages from a plurality of insurance packages offered to medical care providers by the payor server associated with the class of rules; and a rule that applies to specific medical care providers who provide care under one or more specific insurance packages.

5. The method of claim 1, wherein the interacting step farther comprises determining the completed claim submission is associated with the payor server based on information in the completed claim submission.

6. The method of claim 1, further comprising:
   generating remittance advice for the updated completed claim submission;
   parsing an electronic payment; and
   allocating the electronic payment among charge line items for the completed claim submission.

7. The method of claim 6, further comprising:
receiving approval from a medical care provider using the medical practice client for the allocated payments among the charge line items; and
posting the allocated payments to an account of the medical care provider.

8. The method of claim 1, wherein the interacting step further comprises associating a third claim status with the completed claim submission indicative of the completed claim submission comprising a detailed claim error.

9. The method of claim 1, further comprising:
submitting the completed claim submission to the payor server for payment;
associating an alarm with the completed claim submission, the alarm including data indicative of a submission time of the completed claim submission to the payor server; and
if a response from the payor server is not received within a predetermined amount of time from the submission time, triggering the alarm.

10. The method of claim 9, further comprising associating the completed claim submission with a claim inquiry grouping of claims, wherein the claim inquiry grouping of claims comprises claims that need to be followed up on.

11. The method of claim 1, wherein the claim edit screen comprises an explanation portion that denotes an error in the completed claim submission identified by applying the one or more rules from the class of rules associated with the payor server.

12. The method of claim 1, further comprising:
applying the one or more rules from the class of rules associated with the payor server to the completed claim submission; and
associating the second claim status with the completed claim submission if no errors are found by the one or more rules.

13. The method of claim 1, further comprising:
submitting the completed claim submission to the payor server for payment;
receiving a payment from the payor server for the completed claim submission;
applying the payment to the completed claim submission; and
associating a third claim status with the completed claim submission indicative of the payment being applied to the completed claim submission.

14. The method of claim 1, further comprising transmitting data indicative of a claim entry screen to the medical practice client, the claim edit screen comprising (a) a patient claim information section, (b) a procedure section, and (c) a hint section.

15. The method of claim 1, further comprising:
determining if the completed claim submission is billable based on the one or more rules from the class of rules associated with the payor server; and
automatically editing the completed claim submission based on information received from a rules engine, the information comprising edits to be performed to make the completed claim submission billable.

16. The method of claim 1, wherein the interacting step further comprises:
checking a claim rule category and a service date of the completed claim submission; and
defining claim information requirements and claim formatting rules based on the claim rule category and service date, wherein the claim information requirements are used to verify the completed claim submission and the formatting rules are used to format the completed claim submission.

17. The method of claim 1, further comprising transmitting data indicative of a claim review screen to the medical practice client to illustrate one or more errors in the claim, the claim review screen comprising a claim warnings section for denoting one or more warnings associated with the claim, wherein receiving data indicative of the completed claim submission comprises receiving data indicative of changes made by the medical practice client based on the errors denoted in the claim review screen and the claim error explanation portion of the claim edit screen.

18. A computerized method for managing a medical practice comprising:
storing by a medical practice management server in a rules database a plurality of insurance rules comprising one or more classes of rules, each class of rules being associated with one of a plurality of payor servers;
receiving by the medical practice management server data indicative of a completed claim submission for a claim from a medical practice client, the claim being associated with a payor server;
automatically interacting with the completed claim submission by the medical practice management server to correct an error in the completed claim submission, wherein the error is resolved by the medical practice client before processing the completed claim submission, by applying one or more rules from a class of rules associated with the payor server, wherein the one or more rules comprises a new rule, an updated rule, or both received from the payor server, the interacting step comprising:
the medical practice management server automatically associating a first claim status with the completed claim submission indicative of the claim not satisfying one of the one or more rules;
the medical practice management server transmitting data indicative of a claim edit screen to the medical practice client, the claim edit screen comprising a claim edit section for editing the completed claim submission and a claim error explanation portion to explain one or more errors in the completed claim submission to a medical care provider;
the medical practice management server receiving data indicative of an updated completed claim submission from the medical practice client;
the medical practice management server correcting the completed claim submission based on the updated completed claim submission; and
the medical practice management server automatically associating a second claim status with the completed claim submission indicative of the completed claim submission satisfying all of the one or more rules;
the medical practice management server formatting the completed claim submission into information having a form acceptable to the payor server using claim formatting rules;
the medical practice management server transmitting the information to the payor server; and
the medical practice management server automatically associating a third claim status with the completed claim submission indicative of the information being transmitted to the payor server.

19. The method of claim 18, wherein the claim formatting rules are based on a claim rule category and a service date of the completed claim submission.

20. A computerized method for managing a medical practice comprising:

storing by a medical practice management server in a rules database a plurality of insurance rules comprising one or more classes of rules, each class of rules being associated with one of a plurality of payor servers;

receiving data by the medical practice management server indicative of a completed claim submission for a claim from a medical practice client, the claim being associated with a payor server;

automatically interacting with the completed claim submission by the medical practice management server to correct an error in the completed claim submission, wherein the error is resolved by the medical practice client before processing the completed claim submission, by applying one or more rules from a class of rules associated with the payor server, wherein the one or more rules comprises a new rule, an updated rule, or both received from the payor server, the interacting step comprising:

the medical practice management server automatically associating a first claim status with the completed claim submission indicative of the claim not satisfying one of the one or more rules;

the medical practice management server transmitting data indicative of a claim edit screen to the medical practice client, the claim edit screen comprising a claim edit section for editing the completed claim submission and a claim error explanation portion to explain one or more errors in the completed claim submission to a medical care provider;

the medical practice management server receiving data indicative of an updated completed claim submission from the medical practice client;

the medical practice management server correcting the completed claim submission based on the updated completed claim submission; and the medical practice management server automatically associating a second claim status with the completed claim submission indicative of the completed claim submission satisfying all of the one or more rules;

the medical practice management server receiving data indicative of a new rule, an updated rule, or both from the payor server; and the medical practice management server automatically updating the class of rules associated with the payor server to reflect the received data.

* * * * *

UNITED STATES PATENT AND TRADEMARK OFFICE
CERTIFICATE OF CORRECTION

PATENT NO. : 7,617,116 B2
APPLICATION NO. : 09/921654
DATED : November 10, 2009
INVENTOR(S) : Amar et al.

It is certified that error appears in the above-identified patent and that said Letters Patent is hereby corrected as shown below:

Column 20, line 59, delete "farther" and replace it with --further--.

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,617,116 B2 | Page 1 of 1 |
| APPLICATION NO. | : 09/921654 | |
| DATED | : November 10, 2009 | |
| INVENTOR(S) | : Amar et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1262 days.

Signed and Sealed this

Nineteenth Day of October, 2010

David J. Kappos
*Director of the United States Patent and Trademark Office*